US012679883B2

(12) United States Patent
Uda et al.

(10) Patent No.: US 12,679,883 B2
(45) Date of Patent: Jul. 14, 2026

(54) INNOVATIVE PRODUCTION TECHNIQUE FOR ANTIBODY-ENZYME

(71) Applicant: JAPAN SCIENCE AND TECHNOLOGY AGENCY, Saitama (JP)

(72) Inventors: Taizo Uda, Oita (JP); Emi Hifumi, Oita (JP)

(73) Assignee: JAPAN SCIENCE AND TECHNOLOGY AGENCY, Saitama (JP)

(*) Notice: Subject to any disclaimer, the term of this patent is extended or adjusted under 35 U.S.C. 154(b) by 1219 days.

(21) Appl. No.: 17/627,337

(22) PCT Filed: Jul. 22, 2020

(86) PCT No.: PCT/JP2020/028435
§ 371 (c)(1),
(2) Date: Jan. 14, 2022

(87) PCT Pub. No.: WO2021/015237
PCT Pub. Date: Jan. 28, 2021

(65) Prior Publication Data
US 2022/0259290 A1      Aug. 18, 2022

(30) Foreign Application Priority Data

Jul. 24, 2019      (JP) ................................. 2019-136403

(51) Int. Cl.
*C07K 16/06*          (2006.01)
*C07K 1/16*           (2006.01)

(52) U.S. Cl.
CPC ............... *C07K 16/06* (2013.01); *C07K 1/16* (2013.01); *C07K 16/065* (2013.01); *C07K 2317/21* (2013.01)

(58) Field of Classification Search
CPC ............................. C07K 16/065; C07K 16/18; C07K 2317/515; C12N 9/0002
See application file for complete search history.

(56) References Cited

U.S. PATENT DOCUMENTS

| | | | | |
|---|---|---|---|---|
| 8,361,469 B2 * | 1/2013 | Hilden | ...................... | A61P 7/04 |
| | | | | 424/139.1 |
| 10,358,497 B2 * | 7/2019 | Nioi | ................... | A61K 39/3955 |
| 10,633,429 B2 * | 4/2020 | Uda | ...................... | C12N 9/0002 |
| 2012/0322135 A1 | 12/2012 | Uda et al. | | |
| 2015/0064203 A1 | 3/2015 | Uda et al. | | |
| 2019/0256576 A1 | 8/2019 | Uda et al. | | |

FOREIGN PATENT DOCUMENTS

| | | |
|---|---|---|
| JP | 2003-521927 A | 7/2003 |
| JP | 2006-508167 A | 3/2006 |
| JP | 2006-197930 A | 8/2006 |
| JP | 2006347922 A | 12/2006 |
| JP | 2007202443 A | 8/2007 |
| JP | 2007202444 A | 8/2007 |
| JP | 2007202445 A | 8/2007 |
| JP | 2010518815 A | 6/2010 |
| JP | 2011510047 A | 3/2011 |
| JP | 2013-535192 A | 9/2013 |
| JP | 2014503188 A | 2/2014 |
| JP | 2014-506257 A | 3/2014 |
| JP | 2015-501814 A | 1/2015 |
| JP | 2017-519768 A | 7/2017 |
| WO | 0157726 A1 | 8/2001 |
| WO | 2004/050683 A2 | 6/2004 |
| WO | 2011102517 A1 | 8/2011 |
| WO | 2012010562 A1 | 1/2012 |
| WO | 2012094587 A1 | 7/2012 |
| WO | 2012096994 A2 | 7/2012 |
| WO | 2013/085972 A1 | 6/2013 |
| WO | 2013133253 A1 | 9/2013 |
| WO | 2015025786 A1 | 2/2015 |

(Continued)

OTHER PUBLICATIONS

Abdel-Salam et al. Expression of mouse anticreatine kinase (MAK33) monoclonal antibody in the yeast Hansenula polymorpha. Appl Microbiol Biotechnol (2001) 56:157-164. (Year: 2001).*

Japan Patent Office, "International Search Report for PCT Application No. PCT/JP2020/028435", Japan, Sep. 24, 2020.

Emi Hifumi et al., Role of the constant region domain in the structural diversity of human antibody light chains, Faseb Journal, 2017, vol. 31, No. 4, p. 1668-1677.

Emi Hifumi et al., A novel method of preparing the monoform structure of catalytic antibody light chain, Faseb Journal, 2016, vol. 30, No. 2, p. 895-908.

(Continued)

*Primary Examiner* — Shafiqul Haq
(74) *Attorney, Agent, or Firm* — Tim Tingkang Xia, Esq.; Troutman Pepper Locke LLP

(57)          ABSTRACT

A method for producing a κ light chain antibody having enzyme activity or improved enzyme activity includes modifying a polynucleotide that encodes a κ light chain antibody having a polypeptide having an amino acid sequence where the 95th amino acid residue from the N-terminal of a variable region by the Kabat classification is a proline residue, to delete or substitute the proline residue and to obtain a polynucleotide that encodes a κ light chain antibody having a polypeptide having an amino acid sequence where the 95th amino acid residue from the N-terminal of a variable region by the Kabat classification is deleted or substituted with an amino acid residue other than a proline residue, and expressing a κ light chain antibody having enzyme activity in an intracellular or extracellular expression system by using an expression vector including the polynucleotide that encodes a κ light chain antibody obtained after modification.

6 Claims, 9 Drawing Sheets

Specification includes a Sequence Listing.

(56) References Cited

FOREIGN PATENT DOCUMENTS

| WO | 2015196011 A1 | 12/2015 |
| WO | 2019079496 A2 | 4/2019 |

OTHER PUBLICATIONS

Emi Hifumi et al., Method of imparting enzyme action to antibodies, Proceedings of the 28th symposium on biopolymers science, 2018, pp. 147-148.

Taizo Uda et al., Catalytic human antibody light chains capable of cleaving Tau peptides, The 99th Annual Meeting of the Chemical Society of Japan, 2019, 1 F3-49.

Jinquan Luo et al., Coevolution of Antibody Stability and Vk CDR-L3 Canonical Structure, Journal of Molecular Biology, 2010, 402, 708-719.

Certificate of The 12th Symposium on Biorelevant Chemistry, Jun. 28, 2019.

Uda et al., A method for an antibody to possess the enzymatic function (Issue No. 4),2C-09, The 12th Symposium on Biorelevant Chemistry, 2018.

Certificate of The 99th CSJ Annual Meeting, Jun. 28, 2019.

Hifumi et al., A method to possess an enzymatic function to an antibody (5th report) 3G3-19, The 99th CSJ Annual Meeting, 2019.

Japan Patent Office, Office Action issued for Application No. 2021-534071, Japan, Apr. 13, 2024.

* cited by examiner

```
                                                CDR1
                                    1                       33      35
1-39*01        DIQMTQSPSSLSASVGDRVTITCRASQSISSYLNWYQQKPGKA
H55            -------------------------------I-R--V--------

CDR1
                                    1                       34      36
1-5*03         DIQMTQSPSTLSASVGDRVTITCRASQSISSWLAWYQQKPGKA
H34            ------------------------------------------

CDR2
               44     50        57      61              71            81
1-39*01        PKLLIYAASSLQSGVPSRFSGSGSGTDFTLTISSLQPEDFATY
H55            ------------T-----------------------------

CDR2
               44     50        57      61              71            81
1-5*03         PKLLIYDASSLESGVPSRFSGSGSGTDFTLTISSLQPDDFATY
H34            ------K--T--------------------------------

CDR3
               87  89      95
1-39*01        YCQQSYSTP
H55            --------D---RYTFGQGTKLDIK

CDR3
               87  89      95
1-5*03         YCQQYNSYS
H34            ------ST--RTFGQGTKLEIK
```

R-pNA

US 12,679,883 B2

INNOVATIVE PRODUCTION TECHNIQUE FOR ANTIBODY-ENZYME

CROSS-REFERENCE TO RELATED PATENT APPLICATION

This application claims priority to Japanese Patent Application No. 2019-136403 filed Jul. 24, 2019, the content of which is incorporated herein by reference.

FIELD OF THE INVENTION

The present invention relates to an innovative production technique for an antibody-enzyme. Specifically, the present invention relates to a production method for imparting enzyme activity to a κ light chain antibody or improving enzyme activity of a κ light chain antibody.

BACKGROUND OF THE INVENTION

An antibody is composed of heavy chains (H chains) and light chains (L chains). The heavy chains and the light chains are each composed of a variable region (VR) and a constant region (CR), and the variable region has a hypervariable region (CDR: Complementarity Determining Region). Furthermore, the light chains of the antibody are classified into a κ chain and a λ chain.

In recent years, antibodies having enzyme-like activity, that is, antibody-enzymes have drawn attention. Antibody-enzymes have both the high molecular recognition ability and enzyme activity of antibodies. Therefore, the antibody-enzymes are expected to be applied to various fields such as the fields of medicine, and the chemical and food industries. In particular, antibody-enzymes having high specificity to a target molecule and capable of exhibiting inhibitory activity to a target molecule by enzyme activity are expected to be excellent anticancer agents having few side effects. Particularly, human antibody-enzymes are expected to have few side effects when administered to the human body. Accordingly, pharmaceutical companies and the like worldwide are eagerly awaiting the development of useful human antibody-enzymes.

The inventors of the present invention have conducted various investigative studies on antibody-enzymes (for example, see Patent Documents 1 to 4 and the like).

In order for an antibody-enzyme to be clinically used as a pharmaceutical product, it is important that the antibody-enzyme having sufficient activity can be stably mass-produced. However, unfortunately, many antibody-enzymes have insufficient enzyme activity, and antibody-enzymes artificially synthesized by an intracellular or extracellular expression system using gene recombination techniques have performance that is unstable and greatly varies between lots.

CITATION LIST

Patent Documents

Patent Document 1: Japanese Unexamined Patent Application, First Publication No. 2006-197930.
Patent Document 2: PCT International Publication No. WO2011/102517.
Patent Document 3: PCT International Publication No. WO2013/133253.

Patent Document 4: PCT International Publication No. WO2015/025786.

SUMMARY OF THE INVENTION

Technical Problem

The present invention mainly aims to provide a method for producing an antibody-enzyme including an antibody light chain having higher enzyme activity, and a method for stably producing the antibody-enzyme having excellent storage stability.

Solution to the Problem

The inventors of the present invention have found that an antibody light chain having higher enzyme activity can be obtained by a method of deleting or substituting the 95th proline residue from the N-terminal of a variable region in an amino acid sequence of a κ light chain antibody, the variable region according to the Kabat classification, and have accomplished the present invention. Furthermore, the inventors of the present invention have found that a composition containing antibody light chains having higher activity can be obtained by a method of incubating antibody light chains with one or more kinds of metal ions selected from the group consisting of a Group 10 element, a Group 11 element, and a Group 12 element and then removing the metal ions in a purification step in producing antibody light chains, and have accomplished the present invention.

That is, a κ light chain antibody and a production method thereof according to the present invention are described in the following [1] to [12].

[1] A method for producing a κ light chain antibody having enzyme activity or improved enzyme activity, the method including
a modification step of modifying a polynucleotide that encodes a κ light chain antibody having, as a variable region, a polypeptide having an amino acid sequence in which the 95th amino acid residue from the N-terminal of a variable region by the Kabat classification is a proline residue, so as to delete or substitute the proline residue and to obtain a polynucleotide that encodes a κ light chain antibody having, as a variable region, a polypeptide having an amino acid sequence in which the 95th amino acid residue from the N-terminal of a variable region by the Kabat classification is deleted or substituted with an amino acid residue other than a proline residue, and
an expression step of expressing a κ light chain antibody having enzyme activity in an intracellular or extracellular expression system by using an expression vector including the polynucleotide that encodes a κ light chain antibody obtained after the modification step.
[2] The production method described in [1], in which the κ light chain antibody is a human κ light chain antibody or a mouse κ light chain antibody.
[3] The production method described in [1] or [2], in which a variable region of the κ light chain antibody having enzyme activity or improved enzyme activity is a polypeptide selected from the group consisting of the following (1a) to (3c).
(1a) A polypeptide having an amino acid sequence obtained by deletion or substitution of the 95th proline residue from the N-terminal of a variable region by the Kabat classification in an amino acid sequence represented by SEQ ID NO: 1;

(1b) a polypeptide having an amino acid sequence which is obtained by substitution, addition, or deletion of one or more amino acids in the amino acid sequence of the polypeptide (1a) and in which the 95th amino acid residue from the N-terminal of a variable region by the Kabat classification is deleted or substituted with an amino acid residue other than a proline residue;

(1c) a polypeptide having an amino acid sequence which shares 90% or more identity with the amino acid sequence of the polypeptide (1a) and in which the 95th amino acid residue from the N-terminal of a variable region by the Kabat classification is deleted or substituted with an amino acid residue other than a proline residue;

(2a) an amino acid sequence obtained by deletion or substitution of the 95th proline residue from the N-terminal of a variable region by the Kabat classification in an amino acid sequence represented by SEQ ID NO: 2;

(2b) a polypeptide having an amino acid sequence which is obtained by substitution, addition, or deletion of one or more amino acids in the amino acid sequence of the polypeptide (2a) and in which the 95th amino acid residue from the N-terminal of a variable region by the Kabat classification is deleted or substituted with an amino acid residue other than a proline residue;

(2c) a polypeptide having an amino acid sequence which shares 90% or more identity with the amino acid sequence of the polypeptide (2a) and in which the 95th amino acid residue from the N-terminal of a variable region by the Kabat classification is deleted or substituted with an amino acid residue other than a proline residue;

(3a) an amino acid sequence obtained by deletion or substitution of the 95th proline residue from the N-terminal of a variable region by the Kabat classification in an amino acid sequence represented by SEQ ID NO: 3;

(3b) a polypeptide having an amino acid sequence which is obtained by substitution, addition, or deletion of one or more amino acids in the amino acid sequence of the polypeptide (3a) and in which the 95th amino acid residue from the N-terminal of a variable region by the Kabat classification is deleted or substituted with an amino acid residue other than a proline residue;

(3c) a polypeptide having an amino acid sequence which shares 90% or more identity with the amino acid sequence of the polypeptide (3a) and in which the 95th amino acid residue from the N-terminal of a variable region by the Kabat classification is deleted or substituted with an amino acid residue other than a proline residue;

[4] The production method described in any one of [1] to [3], in which a variable region of the κ light chain antibody having enzyme activity or improved enzyme activity is a polypeptide selected from the group consisting of the following (4a) to (7c).

(4a) A polypeptide having an amino acid sequence represented by SEQ ID NO: 4;

(4b) a polypeptide having an amino acid sequence which is obtained by substitution, addition, or deletion of one or more amino acids in the amino acid sequence represented by SEQ ID NO: 4 and in which the 95th amino acid residue from the N-terminal of a variable region by the Kabat classification is deleted or substituted with an amino acid residue other than a proline residue;

(4c) a polypeptide having an amino acid sequence which shares 90% or more identity with the amino acid sequence represented by SEQ ID NO: 4 and in which the 95th amino acid residue from the N-terminal of a variable region by the Kabat classification is deleted or substituted with an amino acid residue other than a proline residue;

(5a) a polypeptide having an amino acid sequence represented by SEQ ID NO: 5;

(5b) a polypeptide having an amino acid sequence which is obtained by substitution, addition, or deletion of one or more amino acids in the amino acid sequence represented by SEQ ID NO: 5 and in which the 95th amino acid residue from the N-terminal of a variable region by the Kabat classification is deleted or substituted with an amino acid residue other than a proline residue;

(5c) a polypeptide having an amino acid sequence which shares 90% or more identity with the amino acid sequence represented by SEQ ID NO: 5 and in which the 95th amino acid residue from the N-terminal of a variable region by the Kabat classification is deleted or substituted with an amino acid residue other than a proline residue;

(6a) a polypeptide having an amino acid sequence represented by SEQ ID NO: 6;

(6b) a polypeptide having an amino acid sequence which is obtained by substitution, addition, or deletion of one or more amino acids in the amino acid sequence represented by SEQ ID NO: 6 and in which the 95th amino acid residue from the N-terminal of a variable region by the Kabat classification is deleted or substituted with an amino acid residue other than a proline residue;

(6c) a polypeptide having an amino acid sequence which shares 90% or more identity with the amino acid sequence represented by SEQ ID NO: 6 and in which the 95th amino acid residue from the N-terminal of a variable region by the Kabat classification is deleted or substituted with an amino acid residue other than a proline residue;

(7a) a polypeptide having an amino acid sequence represented by SEQ ID NO: 7;

(7b) a polypeptide having an amino acid sequence which is obtained by substitution, addition, or deletion of one or more amino acids in the amino acid sequence represented by SEQ ID NO: 7 and in which the 95th amino acid residue from the N-terminal of a variable region by the Kabat classification is deleted or substituted with an amino acid residue other than a proline residue;

(7c) a polypeptide having an amino acid sequence which shares 90% or more identity with the amino acid sequence represented by SEQ ID NO: 7 and in which the 95th amino acid residue from the N-terminal of a variable region by the Kabat classification is deleted or substituted with an amino acid residue other than a proline residue.

[5] The production method described in [1] or [2], in which a variable region of the κ light chain antibody having enzyme activity or improved enzyme activity is a polypeptide selected from the group consisting of the following (8a) to (8c).

(8a) an amino acid sequence obtained by deletion or substitution of the 95th proline residue from the N-terminal of a variable region by the Kabat classification in an amino acid sequence represented by SEQ ID NO: 8;

(8b) a polypeptide having an amino acid sequence which is obtained by substitution, addition, or deletion of one or more amino acids in the amino acid sequence of the polypeptide (8a) and in which the 95th amino acid residue from the N-terminal of a variable region by the Kabat classification is deleted or substituted with an amino acid residue other than a proline residue;

(8c) a polypeptide having an amino acid sequence which shares 90% or more identity with the amino acid sequence of the polypeptide (8a) and in which the 95th amino acid residue from the N-terminal of a variable region by the Kabat classification is deleted or substituted with an amino acid residue other than a proline residue.

[6] The production method described in any one of [1], [2], and [5], in which a variable region of the κ light chain antibody having enzyme activity is a polypeptide selected from the group consisting of the following (9a) to (9c).

(9a) A polypeptide having an amino acid sequence represented by SEQ ID NO: 9;

(9b) a polypeptide having an amino acid sequence which is obtained by substitution, addition, or deletion of one or more amino acids in the amino acid sequence represented by SEQ ID NO: 9 and in which the 95th amino acid residue from the N-terminal of a variable region by the Kabat classification is deleted or substituted with an amino acid residue other than a proline residue;

(9c) a polypeptide having an amino acid sequence which shares 90% or more identity with the amino acid sequence represented by SEQ ID NO: 9 and in which the 95th amino acid residue from the N-terminal of a variable region by the Kabat classification is deleted or substituted with an amino acid residue other than a proline residue.

[7] A method for producing a κ light chain antibody, the method including an expression step of expressing a κ light chain antibody in an intracellular or extracellular expression system by using an expression vector including a polynucleotide that encodes the κ light chain antibody, a first purification step of obtaining a crude purification product containing the κ light chain antibody from an expression product obtained by the expression step by column chromatography using a column containing a first filler, an addition step of adding metal ions to the crude purification product containing the κ light chain antibody so as to obtain a crude purification product containing a κ light chain antibody complex in which the κ light chain antibody and the metal ions are bonded, a second purification step of obtaining a purification product of the κ light chain antibody complex from the crude purification product containing the κ light chain antibody complex obtained after the addition step by column chromatography using a column containing a second filler, and a removal step of removing the metal ions from the purification product of the κ light chain antibody complex obtained after the second purification step so as to obtain a purification product of a κ light chain antibody.

[8] The method for producing a κ light chain antibody described in [7], in which the removal step is performed by adding a chelating agent.

[9] The method for producing a κ light chain antibody described in [7] or [8], in which the metal ions are at least one or more kinds of metal ions selected from the group consisting of a copper ion, a nickel ion, a zinc ion, a gold ion, a silver ion, and a platinum ion.

[10] The method for producing a κ light chain antibody described in any one of [7] to [9], in which a variable region of the κ light chain antibody is a polypeptide having an amino acid sequence in which the 95th amino acid residue from the N-terminal of a variable region by the Kabat classification is deleted or substituted with an amino acid residue other than a proline residue.

[11] The method for producing a κ light chain antibody described in [10], further including, before the expression step, a modification step of modifying a polynucleotide that encodes a κ light chain antibody having, as a variable region, a polypeptide having an amino acid sequence in which the 95th amino acid residue from the N-terminal of a variable region by the Kabat classification is a proline residue, so as to delete or substitute the proline residue and to obtain a polynucleotide that encodes a κ light chain antibody having, as a variable region, a polypeptide having an amino acid sequence in which the 95th amino acid residue from the N-terminal of a variable region by the Kabat classification is deleted or substituted with an amino acid residue other than a proline residue.

[12] A method for imparting enzyme activity to a κ light chain antibody without enzyme activity or improving enzyme activity of a κ light chain antibody, the method including modifying a polynucleotide that encodes the κ light chain antibody without enzyme activity having, as a variable region, a polypeptide having an amino acid sequence in which the 95th amino acid residue from the N-terminal of a variable region by the Kabat classification is a proline residue, so that the proline residue is deleted or substituted.

[13] AK light chain antibody including a polypeptide selected from the group consisting of the following (4a) to (7c) as a variable region.

(4a) A polypeptide having an amino acid sequence represented by SEQ ID NO: 4;

(4b) a polypeptide having an amino acid sequence which is obtained by substitution, addition, or deletion of one or more amino acids in the amino acid sequence represented by SEQ ID NO: 4 and in which the 95th amino acid residue from the N-terminal of a variable region by the Kabat classification is deleted or substituted with an amino acid residue other than a proline residue;

(4c) a polypeptide having an amino acid sequence which shares 90% or more identity with the amino acid sequence represented by SEQ ID NO: 4 and in which the 95th amino acid residue from the N-terminal of a variable region by the Kabat classification is deleted or substituted with an amino acid residue other than a proline residue;

(5a) a polypeptide having an amino acid sequence represented by SEQ ID NO: 5;

(5b) a polypeptide having an amino acid sequence which is obtained by substitution, addition, or deletion of one or more amino acids in the amino acid sequence represented by SEQ ID NO: 5 and in which the 95th amino acid residue from the N-terminal of a variable region by the Kabat classification is deleted or substituted with an amino acid residue other than a proline residue;

(5c) a polypeptide having an amino acid sequence which shares 90% or more identity with the amino acid sequence represented by SEQ ID NO: 5 and in which the 95th amino acid residue from the N-terminal of a variable region by the Kabat classification is deleted or substituted with an amino acid residue other than a proline residue;

(6a) a polypeptide having an amino acid sequence represented by SEQ ID NO: 6;

(6b) a polypeptide having an amino acid sequence which is obtained by substitution, addition, or deletion of one or more amino acids in the amino acid sequence represented by SEQ ID NO: 6 and in which the 95th amino acid residue from the N-terminal of a variable region by the Kabat classification is deleted or substituted with an amino acid residue other than a proline residue;

(6c) a polypeptide having an amino acid sequence which shares 90% or more identity with the amino acid sequence represented by SEQ ID NO: 6 and in which the 95th amino acid residue from the N-terminal of a variable region by the Kabat classification is deleted or substituted with an amino acid residue other than a proline residue;

(7a) a polypeptide having an amino acid sequence represented by SEQ ID NO: 7;

(7b) a polypeptide having an amino acid sequence which is obtained by substitution, addition, or deletion of one or more amino acids in the amino acid sequence represented by SEQ ID NO: 7 and in which the 95th amino acid residue from the N-terminal of a variable region by the Kabat classification is deleted or substituted with an amino acid residue other than a proline residue;

(7c) a polypeptide having an amino acid sequence which shares 90% or more identity with the amino acid sequence represented by SEQ ID NO: 7 and in which the 95th amino acid residue from the N-terminal of a variable region by the Kabat classification is deleted or substituted with an amino acid residue other than a proline residue.

[14] AK light chain antibody including a polypeptide selected from the group consisting of the following (9a) to (9c) as a variable region.

(9a) A polypeptide having an amino acid sequence represented by SEQ ID NO: 9;

(9b) a polypeptide having an amino acid sequence which is obtained by substitution, addition, or deletion of one or more amino acids in the amino acid sequence represented by SEQ ID NO: 9 and in which the 95th amino acid residue from the N-terminal of a variable region by the Kabat classification is deleted or substituted with an amino acid residue other than a proline residue;

(9c) a polypeptide having an amino acid sequence which shares 90% or more identity with the amino acid sequence represented by SEQ ID NO: 9 and in which the 95th amino acid residue from the N-terminal of a variable region by the Kabat classification is deleted or substituted with an amino acid residue other than a proline residue.

Advantageous Effects of the Invention

The κ light chain antibody obtained by the production method according to the present invention has higher enzyme activity compared to the conventional κ light chain antibody, and is expected to be usable as a pharmaceutical product widely applicable to clinical fields.

Furthermore, the method for producing a κ light chain antibody according to the present invention makes it possible to stably produce a highly active κ light chain antibody.

DETAILED DESCRIPTION OF THE INVENTION

Figure 1A:
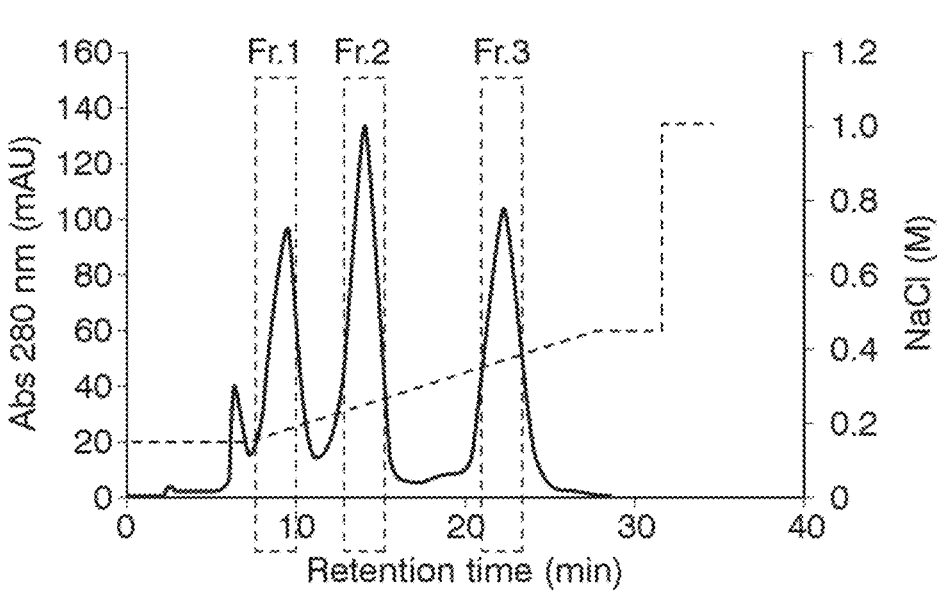
FIG. 1A is a cation exchange chromatogram in a control case (without copper ions added) in Example 1.

In the present invention and present specification, "κ light chain antibody" refers to the κ light chain of an immunoglobulin. The gene of κ light chain antibody is constructed by selecting genes from a group of Vκ genes, a group of Jκ genes, and a group of constant region genes existing in the germline gene and rearranging the genes. The source of the κ light chain antibody is not particularly limited. The κ light chain antibody is preferably derived from a mammal, and more preferably derived from a human or mouse.

In the present invention and present specification, "anti-cancer agent" means an agent having an activity of killing cancer cells or suppressing or inhibiting the growth of cancer cells.

In the related art, it is well known that some amino acids among the amino acid residues that constitute a polypeptide can be easily modified without significantly affecting the structure or function of the polypeptide. Furthermore, it is also well known that in addition to the artificially modified variants, there are also variants of natural proteins that do not significantly change the structure or function of such proteins. In the specification of the present application, the substitution, addition, or deletion of one or more amino acids in a specific amino acid sequence X is described as mutation.

<<Method for Producing κ Light Chain Antibody>>

First Embodiment

The method for producing a κ light chain antibody according to a first embodiment of the present invention (hereinafter, simply described as "production method according to the first embodiment of the present invention" in some cases) is a method for producing a κ light chain antibody having enzyme activity or improved enzyme activity. This method has the following steps in the following order.

A modification step of modifying a polynucleotide that encodes a κ light chain antibody having, as a variable region, a polypeptide having an amino acid sequence in which the 95th amino acid residue from the N-terminal of a variable region by the Kabat classification is a proline residue, so as to delete or substitute the proline residue and to obtain a polynucleotide that encodes a κ light chain antibody having, as a variable region, a polypeptide having an amino acid sequence in which the 95th amino acid residue from the N-terminal of a variable region by the Kabat classification is deleted or substituted with an amino acid residue other than a proline residue, and an expression step of expressing a κ light chain antibody having enzyme activity in an intracellular or extracellular expression system by using an expression vector including the polynucleotide that encodes a κ light chain antibody-obtained after the modification step.

With the production method according to the first embodiment of the present invention, a κ light chain antibody having higher enzyme activity compared to the conventional κ light chain antibody can be obtained.

Hereinafter, details of each configuration of the production method according to the first embodiment of the present invention will be described.

<Modification Step>

The modification step is a step of modifying a polynucleotide that encodes a κ light chain antibody having, as a variable region, a polypeptide having an amino acid sequence in which the 95th amino acid residue from the N-terminal of a variable region by the Kabat classification is a proline residue, so as to delete or substitute the proline residue and to obtain a polynucleotide that encodes a κ light chain antibody having, as a variable region, a polypeptide having an amino acid sequence in which the 95th amino acid residue from the N-terminal of a variable region by the Kabat classification is deleted or substituted with an amino acid residue other than a proline residue.

Performing this step makes it possible to impart enzyme activity to a κ light chain antibody without enzyme activity or to improve enzyme activity of a κ light chain antibody that exhibits low activity. That is, this step can also be called "method for imparting enzyme activity to a κ light chain antibody without enzyme activity" or "method for improving enzyme activity of a κ light chain antibody"

Improving enzyme activity of a κ light chain antibody means that the enzyme activity of a κ light chain antibody after modification is improved 10%, 20%, 30%, 40%, 50%, 60%, 70%, 80%, 90%, 100%, 200%, or 300% or more compared to the enzyme activity of a κ light chain antibody before modification.

The modification for deleting or substituting the proline residue can be easily performed by a method of mutating a proline residue at the 95th position from the N-terminal of a variable region by the Kabat classification in the amino acid sequence of a variable region by using a known technique, among the amino acid residues constituting a polypeptide. For example, by a known point mutation introduction method, any base of a polynucleotide encoding a polypeptide can be mutated. In addition, it is possible to prepare a deletion variant or a substitution variant by designing a primer corresponding to any site of a polynucleotide encoding a polypeptide.

<Expression Step>

The expression step is a step of expressing a κ light chain antibody in an expression system known in the related art, such as an intracellular or extracellular expression system, by using an expression vector including the polynucleotide that encodes a κ light chain antibody obtained after the modification step.

In a case where a recombinant expression system is used, for example, it is possible to adopt a method of incorporating the polynucleotide that encodes the κ light chain antibody according to the present invention into a recombinant expression vector, then introducing the expression vector into a host that can express the polynucleotide by a known method, and purifying the polypeptide produced in the host (transformant) by translation. The recombinant expression vector may or may not be a plasmid, as long as the target polynucleotide can be introduced into the host.

In a case where a foreign polynucleotide is introduced into a host as described above, it is preferable that a promoter functioning in the host to induce expression of the foreign polynucleotide be incorporated into the expression vector. Although the method for purifying the recombinantly produced polypeptide varies with the host to be used and the properties of the polypeptide, it is possible to relatively easily purify the target polypeptide by using a tag or the like.

In a case where a cell-free expression system (cell-free protein synthesis system) is used, it is preferable to use a method of adding the polynucleotide that encodes the κ light chain antibody according to the present invention to a solution containing components necessary for translation•synthesis of proteins such as ribosomes or t-RNA, incubating the solution at an appropriate temperature, and purifying the synthesized polypeptide.

Examples of the cell-free protein synthesis system include a system using a wheat germ extract, a system using a rabbit reticulocyte extract, a system using an *E. coli* S30 extract, and a system using a cell component extract obtained from a plant protoplast from which vacuole has been removed. Generally, for the translation of genes derived from eukaryotes, a system of eukaryotic cells, that is, either a system using wheat germ extract or a system using a rabbit reticulocyte extract is selected. Considering the gene source (prokaryote/eukaryote) to be translated or the purpose of use of the synthesized protein, any of the above synthesis systems may be selected. As these synthesis systems, various commercially available kits can be used.

Many virus-derived gene products exhibit activity through a complicated biochemical reaction involved in the intracellular membrane of the endoplasmic reticulum, Golgi apparatus, and the like after the translation thereof. Therefore, in order to reproduce various biochemical reactions in a test tube, an intracellular membrane component (for example, a microsomal membrane) needs to be added. The cell component extract obtained from the plant protoplast from which vacuole has been removed is preferable, because this extract can be used as a cell-free protein synthesis liquid containing intracellular membrane components and does not require the addition of microsomal membrane.

"Intracellular membrane components" used in the present specification means cell organelles (that is, general intracellular organelles such as endoplasmic reticulum, Golgi apparatus, mitochondria, chloroplasts, and vacuoles) formed of a lipid membrane in the cytoplasm. Particularly, the endoplasmic reticulum and the Golgi apparatus play important roles in post-translational modification of proteins, and are essential cell components for the maturation of membrane proteins and secretory proteins.

In addition, the κ light chain antibody according to the present invention can also be derived from cells or tissues that naturally express the κ light chain antibody. For example, it is possible to identify cells or tissues that naturally express the κ light chain antibody according to the present invention by using antibodies or oligonucleotides.

In addition, the κ light chain antibody according to the present invention can also be chemically synthesized. The chemical synthesis method is not particularly limited, and any of the methods used for chemically synthesizing a polypeptide may be adopted.

The production method according to the first embodiment of the present invention can further include other steps such as a purification step. The purification step can be appropriately carried out by using a known antibody purification method. For example, it is also possible to use a purification method including a first purification step, an addition step, and a second purification step. Details of these steps will be described later.

Second Embodiment

The method for producing a κ light chain antibody according to a second embodiment of the present invention (hereinafter, simply described as "production method according to the second embodiment of the present invention" in some cases) includes the following steps in the following order.

An expression step of expressing a κ light chain antibody in an intracellular or extracellular expression system by using an expression•vector including a polynucleotide that encodes the κ light chain antibody;

a first purification step of obtaining a crude purification product containing the κ light chain antibody from an expression product obtained by the expression step by column chromatography using a column containing a first filler;

an addition step of adding metal ions to the crude purification product containing the κ light chain antibody so as to obtain a κ light chain antibody complex in which the κ light chain antibody and the metal ions are bonded;

a second purification step of obtaining a purification product of the κ light chain antibody complex from the crude purification product containing the κ light chain antibody complex obtained after the addition step by column chromatography using a column containing a second filler; and a removal step of removing the metal ions from the purification product of the κ light chain antibody complex obtained after the second purification step so as to obtain a purification product of a κ light chain antibody.

The production method according to the second embodiment of the present invention is not limited to a κ light chain antibody having, as a variable region, a polypeptide having an amino acid sequence in which the 95th amino acid residue from the N-terminal of a variable region by the Kabat classification is deleted or substituted with an amino acid residue other than a proline residue. The production method can also be applied to other κ light chain antibodies. With the production method according to the second embodiment of the present invention, it is possible to stably produce an antibody-enzyme having excellent storage stability.

Hereinafter, each step will be specifically described.

<Expression Step>

The expression step is a step of expressing a κ light chain antibody in an expression system known in the related art, such as an intracellular or extracellular expression system, by using an expression vector including a polynucleotide that encodes the κ light chain antibody.

In a case where a recombinant expression system is used, for example, it is possible to adopt a method of incorporating the polynucleotide that encodes the κ light chain antibody according to the present invention into a recombinant expression vector, then introducing the expression vector into a host that can express the polynucleotide by a known method, and purifying the polypeptide produced in the host (transformant) by translation. The recombinant expression vector may or may not be a plasmid, as long as the target polynucleotide can be introduced into the host.

In a case where a foreign polynucleotide is introduced into a host as described above, it is preferable that a promoter functioning in the host to induce expression of the foreign polynucleotide be incorporated into the expression vector. Although the method for purifying the recombinantly produced polypeptide varies with the host to be used and the properties of the polypeptide, it is possible to relatively easily purify the target polypeptide by using a tag or the like.

In a case where a cell-free expression system (cell-free protein synthesis system) is used, it is preferable to use a method of adding the polynucleotide that encodes the κ light chain antibody according to the present invention to a solution containing components necessary for translation•synthesis of proteins such as ribosomes or t-RNA, incubating the solution at an appropriate temperature, and purifying the synthesized polypeptide.

Examples of the cell-free protein synthesis system include a system using a wheat germ extract, a system using a rabbit reticulocyte extract, a system using an *E. coli* S30 extract, and a system using a cell component extract obtained from a plant protoplast from which vacuole has been removed. Generally, for the translation of genes derived from eukaryotes, a system of eukaryotic cells, that is, either a system using wheat germ extract or a system using a rabbit reticulocyte extract is selected. Considering the gene source (prokaryote/eukaryote) to be translated or the purpose of use of the synthesized protein, any of the above synthesis systems may be selected. As these synthesis systems, various commercially available kits can be used.

Many virus-derived gene products exhibit activity through a complicated biochemical reaction involved in the intracellular membrane of the endoplasmic reticulum, Golgi apparatus, and the like after the translation thereof. Therefore, in order to reproduce various biochemical reactions in a test tube, an intracellular membrane component (for example, a microsomal membrane) needs to be added. The cell component extract obtained from the plant protoplast from which vacuole has been removed is preferable, because this extract can be used as a cell-free protein synthesis liquid containing intracellular membrane components and does not require the addition of microsomal membrane.

"Intracellular membrane components" used in the present specification means cell organelles (that is, general intracellular organelles such as endoplasmic reticulum, Golgi apparatus, mitochondria, chloroplasts, and vacuoles) formed of a lipid membrane in the cytoplasm. Particularly, the endoplasmic reticulum and the Golgi apparatus play important roles in post-translational modification of proteins, and are essential cell components for the maturation of membrane proteins and secretory proteins.

In addition, the κ light chain antibody according to the present invention can also be derived from cells or tissues that naturally express the κ light chain antibody. For example, it is possible to identify cells or tissues that naturally express the κ light chain antibody according to the present invention by using antibodies or oligonucleotides.

In addition, the κ light chain antibody according to the present invention can also be chemically synthesized. The chemical synthesis method is not particularly limited, and any of the methods used for chemically synthesizing a polypeptide may be adopted.

<First Purification Step>

The first purification step is a step of obtaining a crude purification product containing the κ light chain antibody from an expression product obtained by the expression step by column chromatography using a column containing a first filler.

As the method for purifying the κ light chain antibody from the expression product obtained by the expression step, it is preferable to use a method of preparing a cell extract from a cell or tissue by a known method (for example, a method of disrupting a cell or tissue, then centrifuging the resultant, and recovering a soluble fraction) and then purifying the κ light chain antibody from the cell extract by a known method (for example, ammonium sulfate precipitation or ethanol precipitation, acid extraction, anion or cation exchange chromatography, phosphocellulose chromatography, hydrophobic interaction chromatography, affinity chromatography, hydroxyapatite chromatography, or lectin chromatography). However, the purification method is not limited thereto. For purification, high-performance liquid chromatography ("HPLC") is most preferably used.

<Addition Step>

The addition step is a step of adding metal ions to the crude purification product containing the κ light chain antibody so as to obtain a κ light chain antibody complex in which the κ light chain antibody and the metal ions are bonded. By adding metal ions to a crude composition containing the κ light chain antibody, it is possible to easily obtain a κ light chain antibody dimer and to stably produce the κ light chain antibody while maintaining the enzyme activity thereof.

In the present invention, the metal ions to be bonded to the κ light chain antibody are one or more kinds of metal ions selected from the group consisting of a Group 10 element, a Group 11 element, and a Group 12 element. Only one kind of metal ions may be bonded to the κ light chain antibody, or two or more kinds of metal ions may be bonded to the κ light chain antibody in combination. The metal ions are preferably one or more kinds of metal ions selected from the group consisting of a copper ion, a nickel ion, a zinc ion, a gold ion, a silver ion, and a platinum ion in view of safety to the living body, more preferably one or more kinds of metal ions selected from the group consisting of a copper ion, a nickel ion, and a zinc ion in view of mass production, and even more preferably copper ions in view of further improving the activity of the κ light chain antibody on the living body.

Examples of the method of adding metal ions to the crude composition containing the κ light chain antibody include a method of incubating the κ light chain antibody according to the present invention in a solution containing the metal ions. The metal ions may be incubated in a solution in which a dimer and a monomer of the κ light chain antibody are mixed together. Alternatively, the κ light chain antibody purified to include either of the dimer or monomer may be incubated with the metal ions.

The incubation time of the κ light chain antibody according to the present invention and the metal ions can be appropriately determined in consideration of the type of κ light chain antibody, the type of metal ions, the solvent, the incubation temperature, and the like so that a sufficient amount of metal ions can bind to the κ light chain antibody. For example, the incubation can be performed for 30 minutes to 48 hours at room temperature. It is preferable that the incubated resultant be subjected to the subsequent second purification step.

<Second Purification Step>

The second purification step is a step of obtaining a purification product of a κ light chain antibody complex from the crude purification product containing the κ light chain antibody complex obtained after the addition step by column chromatography using a column containing a second filler.

Examples of the method for purifying the purification product of the κ light chain antibody complex from the crude purification product containing the κ light chain antibody complex in the second purification step are the same as the methods exemplified above regarding the first purification step. For purification, high-performance liquid chromatography ("HPLC") is most preferably used.

The combination of the first filler in the first purification step and the second filler in the second purification step is not particularly limited, as long as the finally obtained κ light chain antibody can have a desired degree of purification. The combination can be appropriately determined in consideration of the type of κ light chain antibody, whether or not addition modification is to be performed, and the like. For example, in a case where the κ light chain antibody synthesized using an expression system is an epitope-labeled polypeptide fused with a His tag or the like, it is preferable to use a filler having high affinity for the labeled epitope as the first filler and to use anion or cation exchange chromatography as the second filler. In this case, it is possible to purify the κ light chain antibody in the first purification step, and to separate or fractionate a monomer and a dimer or to fractionate the antibody based on whether or not the antibody is bonded to metal ions in the second purification step.

<Removal Step>

The removal step is a step of removing the metal ions from the purification product of the κ light chain antibody complex obtained after the second purification step so as to obtain a purification product of a κ light chain antibody. By removing the metal ions from the purification product of the κ light chain antibody complex, it is possible to improve the storage stability of the κ light chain antibody as shown in Examples that will be described later.

Examples of the method of removing the metal ions from the purification product of the κ light chain antibody complex include a method of incubating the purification product of the κ light chain antibody complex in a solution containing a chelating agent, and the like.

Examples of the chelating agent used in the removal step include ethylenediaminetetraacetic acid (EDTA), citric acid, phytic acid, and the like.

The production method according to the second embodiment of the present invention may include other steps in addition to the above steps.

For example, in a case where the production method according to the second embodiment of the present invention is used to produce a κ light chain antibody having, as the aforementioned variable region, a polypeptide having an amino acid sequence in which the 95th amino acid residue from the N-terminal of a variable region by the Kabat classification is deleted or substituted with an amino acid residue other than a proline residue, the production method may further include a modification step.

<Modification Step>

The modification step is a step of modifying, before the expression step, a polynucleotide that encodes a κ light chain antibody having, as a variable region, a polypeptide having an amino acid sequence in which the 95th amino acid residue from the N-terminal of a variable region by the Kabat classification is a proline residue, so as to delete or substitute the proline residue and to obtain a polynucleotide that encodes a κ light chain antibody having, as a variable region, a polypeptide having an amino acid sequence in which the 95th amino acid residue from the N-terminal of a variable region by the Kabat classification is deleted or substituted with an amino acid residue other than a proline residue.

The modification for deleting or substituting the proline residue can be easily performed by a method of mutating a proline residue at the 95th position from the N-terminal of a variable region by the Kabat classification in the amino acid sequence of a variable region by using a known technique, among the amino acid residues constituting a polypeptide. For example, by a known point mutation introduction method, any base of a polynucleotide encoding a polypeptide can be mutated. In addition, it is possible to prepare a deletion variant or a substitution variant by designing a primer corresponding to any site of a polynucleotide encoding a polypeptide.

<<κ Light Chain Antibody>>

The κ light chain antibody according to the present invention has, as a variable region, a polypeptide having an amino acid sequence in which the 95th amino acid residue from the N-terminal of a variable region by the Kabat classification is deleted or substituted with an amino acid residue other than a proline residue. The κ light chain antibody according to the present invention is an antibody-enzyme and has higher enzyme activity compared to the conventional antibody-enzymes. That is, the antibody-enzyme according to the present invention consists of a κ light chain antibody having, as a variable region, a polypeptide having an amino acid sequence in which the 95th amino acid residue from the N-terminal of a variable region by the Kabat classification is deleted or substituted with an amino acid residue other than a proline residue. This antibody-enzyme exhibits enzyme activity by using the recognized antigen as a substrate. The κ light chain antibody according to the present invention can be produced by "method for producing a κ light chain antibody" described above.

Hereinafter, the κ light chain antibody according to the present invention will be called "proline deletant" in some cases. The proline deletant in the present specification is a peptide having, as a variable region, a peptide having an amino acid sequence in which the 95th amino acid residue from the N-terminal of a variable region by the Kabat classification is not a proline residue. The proline deletant may be a wild-type κ light chain antibody from which a proline residue has been deleted or in which a proline residue has been substituted with another amino acid residue.

The amino acid sequence numbering by the Kabat classification can be carried out, for example, by analyzing the amino acid sequence of an antibody according to the Kabat numbering system by using abYsis software (URL; http://www.abysis.org/).

The κ light chain antibody according to the present invention is not particularly limited as long as it has the configuration described above. In view of medical applicability, it is preferable that the κ light chain antibody have a catalytic triad-like structure. The catalytic triad-like structure is a structure that is formed of, for example, a serine residue, a histidine residue, and an asparagine residue and is considered to have catalytic activity. Examples of the κ light chain antibody having a catalytic triad-like structure include a κ light chain antibody that has a Vκ gene belonging to subgroup II or a Vκ gene belonging to another subgroup such as subgroup I, a κ light chain antibody that has at least a variable region of these, and variants of these. For example, as disclosed in Patent Document 2, a wild-type κ light chain antibody can be obtained by PCR and the like using a nucleic acid derived from a biosample (such as a lymphocyte) collected from a human as a template. It is also possible to obtain various variants from the obtained wild-type by a known gene recombination technique.

It is particularly preferable that the κ light chain antibody according to the present invention have at least any of protease activity, amidase activity, nucleolytic activity, cytotoxicity against cancer cells, and antiviral activity. The κ light chain antibody having these activities is particularly useful as an anticancer agent, an antiviral agent, or the like.

By having cysteine for forming a disulfide bond, the wild-type κ light chain antibody forms a dimer. A κ light chain antibody variant in which the cysteine has been substituted with another amino acid (such as alanine) cannot form a dimer and is in the form of a monomer. The κ light chain antibody according to the present invention may be a monomer or form a dimer. Depending on the type of κ light chain antibody, sometimes a dimer has higher activity, such as protease activity, compared to a monomer. In this case, the κ light chain antibody forming a dimer is preferable.

The variable region of the κ light chain antibody (proline deletant) according to the present invention is preferably a polypeptide selected from the group consisting of the following (1a) to (3c).

(1a) A polypeptide having an amino acid sequence obtained by deletion or substitution of the 100th proline residue from the N-terminal (95th proline residue from the N-terminal of a variable region by the Kabat classification) in an amino acid sequence represented by SEQ ID NO: 1;

(1b) a polypeptide having an amino acid sequence which is obtained by substitution, addition, or deletion of one or more amino acids in the amino acid sequence of the polypeptide (1a) and in which the 95th amino acid residue from the N-terminal of a variable region by the Kabat classification is deleted or substituted with an amino acid residue other than a proline residue;

(1c) a polypeptide having an amino acid sequence which shares 90% or more identity with the amino acid sequence of the polypeptide (1a) and in which the 95th amino acid residue from the N-terminal of a variable region by the Kabat classification is deleted or substituted with an amino acid residue other than a proline residue;

(2a) an amino acid sequence obtained by deletion or substitution of the 100th proline residue from the N-terminal (95th proline residue from the N-terminal of a variable region by the Kabat classification) in an amino acid sequence represented by SEQ ID NO: 2;

(2b) a polypeptide having an amino acid sequence which is obtained by substitution, addition, or deletion of one or more amino acids in the amino acid sequence of the polypeptide (2a) and in which the 95th amino acid residue from the N-terminal of a variable region by the Kabat classification is deleted or substituted with an amino acid residue other than a proline residue;

(2c) a polypeptide having an amino acid sequence which shares 90% or more identity with the amino acid sequence of the polypeptide (2a) and in which the 95th amino acid residue from the N-terminal of a variable region by the Kabat classification is deleted or substituted with an amino acid residue other than a proline residue;

(3a) an amino acid sequence obtained by deletion or substitution of the 100th proline residue from the N-terminal (95th proline residue from the N-terminal of a variable region by the Kabat classification) in an amino acid sequence represented by SEQ ID NO: 3;

(3b) a polypeptide having an amino acid sequence which is obtained by substitution, addition, or deletion of one or more amino acids in the amino acid sequence of the polypeptide (3a) and in which the 95th amino acid residue from the N-terminal of a variable region by the Kabat classification is deleted or substituted with an amino acid residue other than a proline residue;

(3c) a polypeptide having an amino acid sequence which shares 90% or more identity with the amino acid sequence of the polypeptide (3a) and in which the 95th amino acid residue by the Kabat classification from the N-terminal of the variable region is deleted or substituted with an amino acid residue other than a proline residue.

In the polypeptides (1a) to (3c), the amino acid residue that can substitute for the 95th proline residue from the N-terminal of a variable region by the Kabat classification is not particularly limited, as long as the amino acid residue has a side chain that is less bulky than that of the proline residue and does not interrupt the catalytic triad-like structure. Examples of such an amino acid residue include lysine, arginine, histidine, aspartic acid, glutamic acid, serine, threonine, asparagine, glutamine, alanine, glycine, valine, isoleucine, leucine, methionine, cysteine, and the like. Among these, serine or arginine is preferable.

The sequence identity of a target amino acid sequence with respect to the reference amino acid sequence can be determined as follows, for example. First, the reference amino acid sequence and the target amino acid sequence are aligned. At this time, each of the amino acid sequences may include a gap so as to maximize the sequence identity. Then, by counting the number of identical amino acids in the reference amino acid sequence and the target amino acid sequence, it is possible to determine the sequence identity according to the following formula.

$$\text{"Sequence identity (\%)"} = [\text{number of identical amino acids}]/[\text{total number of amino acids in target amino acid sequence}] \times 100$$

The human κ light chain antibody having, as a variable region, a polypeptide having the amino acid sequence represented by SEQ ID NO:1 is also called "human κ light chain antibody (S35)" in some cases. The human κ light chain antibody (S35) can be obtained by adding a known human antibody constant region to the variable region described above. In one embodiment, the full-length amino acid sequence of S35 is represented by SEQ ID NO: 10. In the human κ light chain antibody (S35), CDR1 consists of the 24th to 39th amino acids in the amino acid sequences represented by SEQ ID NOs: 1 and 10, CDR2 consists of the 55th to 61st amino acids in the amino acid sequences represented by SEQ ID NOs: 1 and 10, and CDR3 consists of the 94th to 102nd amino acids in the amino acid sequences represented by SEQ ID NOs: 1 and 10. In addition, the 219th cysteine in the amino acid sequence represented by SEQ ID NO: 10 is cysteine for forming a disulfide bond with other light chains.

As will be shown in Examples later, the human κ light chain antibody (S35) does not have degradation activity on an antigen peptide having an amino acid sequence consisting of the 26th to 33rd amino acids from the N-terminal of amyloid β (hereinafter, this antigen peptide will be called "Aβ peptide" in some cases). However, the human κ light chain antibody including a variable region having an amino acid sequence which is obtained by deletion or substitution of the 95th proline residue from the N-terminal of a variable region by the Kabat classification in the amino acid sequence represented by SEQ ID NO:1, that is, the human κ light chain antibody having the polypeptide (1a) as a variable region (hereinafter, called "proline deletant of the human κ light chain antibody (S35)" in some cases) can exhibit degradation activity on the Aβ peptide. Therefore, the proline deletant of the human κ light chain antibody (S35) is suitable as an active ingredient of an anti-amyloid β (Aβ) degrading agent. In order for the proline deletant of the human κ light chain antibody (S35) to exhibit anti-Aβ degradation activity, it is important for this protein to have a high ability to recognize a target molecule. Therefore, in the proline deletant of the human κ light chain antibody (S35), the variable region, particularly, the CDR sequence is the active center of the anti-amyloid β degradation activity.

The proline deletant of the human κ light chain antibody (S35) may be a variant having a mutation that may not impair the enzyme activity. Particularly, as the variant of the proline deletant of the human κ light chain antibody (S35), a variant having a mutation in a region other than a variable region is preferable, and a variant is more preferable in which CDR1 and CDR2 are identical to (conserved as) the amino acid sequence represented by SEQ ID NO: 1 or 10, the C-terminal proline residue of CDR3 is deleted or substituted but the amino acid sequence of CDR3 is identical (conversed) except for the proline residue, and amino acids other than the CDR regions in the variable region may be mutated from the human κ light chain antibody (S35). Examples of the variant of the proline deletant of the human κ light chain antibody (S35) include a human κ light chain antibody having the aforementioned polypeptide (1b) or (1c) as a variable region, and the like.

In the polypeptide (1b), the number of amino acids that may be deleted, substituted, or added is preferably 1 or more and 5 or less, more preferably 1 or more and 2 or less, and even more preferably 1. Hereinafter, the same shall be applied to proline deletant variants having the aforementioned polypeptide (2b) or (3b) and the like as a variable region.

Examples of commonly possible amino acid substitution include alanine/serine, valine/isoleucine, aspartic acid/glutamic acid, threonine/serine, alanine/glycine, alanine/threonine, serine/asparagine, alanine/valine, serine/glycine, tyrosine/phenylalanine, alanine/proline, lysine/arginine, aspartic acid/asparagine, leucine/isoleucine, leucine/valine, alanine/glutamic acid, aspartic acid/glycine, and the like.

In order for the polypeptide of (1c) to be functionally equivalent to the polypeptide having the amino acid sequence of (1a), the polypeptide (1a) does not have the 95th proline residue from the N-terminal of a variable region by the Kabat classification in the amino acid sequence represented by SEQ ID NO: 1 just as the polypeptide (1a), and the identity between the amino acid sequence of the polypeptide (1c) and the amino acid sequence of the polypeptide (1a) is 90% or more, preferably 95% or more, even more preferably 97% or more, and still more preferably 99% or more. Hereinafter, the same shall be applied to proline deletant variants having the aforementioned polypeptide (2c) or (3c) and the like as a variable region.

Examples of the proline deletant of the human κ light chain antibody (S35) also include a polypeptide represented by an amino acid sequence obtained by deletion of the 95th proline residue and substitution of the 219th cysteine with alanine in the amino acid sequence represented by SEQ ID NO: 10, and the like.

The human κ light chain antibody having, as a variable region, a polypeptide having the amino acid sequence represented by SEQ ID NO:2 is also called "human κ light chain antibody (T99)" in some cases. The human κ light chain antibody (T99) can be obtained by adding a known human antibody constant region to the variable region described above. In one embodiment, the full-length amino acid sequence of T99 is represented by SEQ ID NO: 13. In the human κ light chain antibody (T99), CDR1 consists of the 24th to 39th amino acids in the amino acid sequences represented by SEQ ID NOs: 2 and 13, CDR2 consists of the 55th to 61st amino acids in the amino acid sequences represented by SEQ ID NOs: 2 and 13, and CDR3 consists of the 94th to 102nd amino acids in the amino acid sequences represented by SEQ ID NOs: 2 and 13. In addition, the 219th cysteine in the amino acid sequence represented by SEQ ID NO: 13 is cysteine for forming a disulfide bond with other light chains.

As will be shown in Examples later, the human κ light chain antibody (T99) does not have degradation activity on the Aβ peptide. However, the human κ light chain antibody including a variable region having an amino acid sequence which is obtained by deletion of substitution of the 95th proline residue from the N-terminal of a variable region by the Kabat classification in the amino acid sequence represented by SEQ ID NO:2, that is, the human κ light chain antibody having the polypeptide (2a) as a variable region (hereinafter, called "proline deletant of the human κ light chain antibody (T99)" in some cases) can exhibit degradation activity on the Aβ peptide. Therefore, the proline deletant of the human κ light chain antibody (T99) is suitable as an active ingredient of an anti-Aβ degrading agent. In order for the proline deletant of the human κ light chain antibody (T99) to exhibit anti-Aβ degradation activity, it is important for this protein to have a high ability to recognize a target molecule. Therefore, in the proline deletant of the human κ light chain antibody (T99), the variable region, particularly, the CDR sequence is the active center of the anti-amyloid β degradation activity.

The proline deletant of the human κ light chain antibody (T99) may be a variant having a mutation that may not impair the enzyme activity. Particularly, as the variant of the proline deletant of the human κ light chain antibody (T99), a variant having a mutation in a region other than a variable region is preferable, and a variant is more preferable in which CDR1 and CDR2 are identical to (conserved as) the amino acid sequence represented by SEQ ID NO: 2 or 13, the C-terminal proline residue of CDR3 is deleted or substituted but the amino acid sequence of CDR3 is identical (conversed) except for the proline residue, and amino acids other than the CDR regions in the variable region may be mutated from the human κ light chain antibody (T99). Examples of the variant of the proline deletant of the human κ light chain antibody (T99) include a human κ light chain antibody having the polypeptide (2b) or (2c) as a variable region, and the like.

Examples of the variant of the proline deletant of the human κ light chain antibody (T99) also include a polypeptide having an amino acid obtained by deletion of the 95th proline residue and substitution of the 219th cysteine with alanine in the amino acid sequence represented by SEQ ID NO: 13, and the like.

The human κ light chain antibody having, as a variable region, a polypeptide having the amino acid sequence represented by SEQ ID NO:3 is also called "human κ light chain antibody (H55)" in some cases. The human κ light chain antibody (H55) can be obtained by adding a known human antibody constant region to the variable region described above. In one embodiment, the full-length amino acid sequence of T55 is represented by SEQ ID NO: 15. In the human κ light chain antibody (H55), CDR1 consists of the 24th to 39th amino acids in the amino acid sequences represented by SEQ ID NOs: 3 and 15, CDR2 consists of the 55th to 61st amino acids in the amino acid sequences represented by SEQ ID NOs: 3 and 15, and CDR3 consists of the 94th to 103rd amino acids in the amino acid sequences represented by SEQ ID NOs: 3 and 15. In addition, the 215th cysteine in the amino acid sequence represented by SEQ ID NO: 15 is cysteine for forming a disulfide bond with other light chains.

As will be shown in Examples later, the human κ light chain antibody (H55) does not have degradation activity on an antigen peptide (hereinafter, called "PD-1 peptide" in some cases) having an amino acid sequence consisting of the 124th to 141st amino acids from the N-terminal of PD-1, which is an immune checkpoint receptor on the surface of cytotoxic T cells. However, the human κ light chain antibody (hereinafter, called "proline deletant of the human κ light chain antibody (H55)" in some cases) including a variable region having an amino acid sequence which is obtained by deletion or substitution of the 95th proline residue from the N-terminal of a variable region by the Kabat classification in the amino acid sequence represented by SEQ ID NO: 3 can exhibit degradation activity on the PD-1 peptide. Therefore, the proline deletant of the human κ light chain antibody (H55) is suitable as an active ingredient of an anticancer agent. In order for the proline deletant of the human κ light chain antibody (H55) to exhibit anticancer activity, it is important for this protein to have a high ability to recognize a target molecule. Therefore, in the proline deletant of the human κ light chain antibody (H55), the variable region, particularly, the CDR sequence is the active center of the anticancer activity.

The proline deletant of the human κ light chain antibody (H55) may be a variant having a mutation that may not impair the enzyme activity. Particularly, as the variant of the proline deletant of the human κ light chain antibody (H55), a variant having a mutation in a region other than a variable region is preferable, and a variant is more preferable in which CDR1 and CDR2 are identical to (conserved as) the amino acid sequence represented by SEQ ID NO: 3 or 15, the C-terminal proline residue of CDR3 is deleted or substituted but the amino acid sequence of CDR3 is identical (conversed) except for the proline residue, and amino acids other than the CDR regions in the variable region may be mutated from the human κ light chain antibody (H55). Examples of the variant of the proline deletant of the human κ light chain antibody (H55) include a human κ light chain antibody having the polypeptide (3b) or (3c) as a variable region.

Examples of the variant of the proline deletant of the human κ light chain antibody (H55) also include a polypeptide having an amino acid sequence obtained by deletion of the 95th proline residue and substitution of the 215th cysteine with alanine in the amino acid sequence represented by SEQ ID NO: 15, and the like.

The variable region of the κ light chain antibody (proline deletant) according to the present invention is more preferably a polypeptide selected from the group consisting of the following (4a) to (7c).

(4a) A polypeptide having an amino acid sequence represented by SEQ ID NO: 4;

(4b) a polypeptide having an amino acid sequence which is obtained by substitution, addition, or deletion of one or more amino acids in the amino acid sequence represented by SEQ ID NO: 4 and in which the 95th amino acid residue from the N-terminal of a variable region by the Kabat classification is deleted or substituted with an amino acid residue other than a proline residue;

(4c) a polypeptide having an amino acid sequence which shares 90% or more identity with the amino acid sequence represented by SEQ ID NO: 4 and in which the 95th amino acid residue from the N-terminal of a variable region by the Kabat classification is deleted or substituted with an amino acid residue other than a proline residue;

(5a) a polypeptide having an amino acid sequence represented by SEQ ID NO: 5;

(5b) a polypeptide having an amino acid sequence which is obtained by substitution, addition, or deletion of one or more amino acids in the amino acid sequence represented by SEQ ID NO: 5 and in which the 95th amino acid residue from the N-terminal of a variable region by the Kabat classification is deleted or substituted with an amino acid residue other than a proline residue;

(5c) a polypeptide having an amino acid sequence which shares 90% or more identity with the amino acid sequence represented by SEQ ID NO: 5 and in which the 95th amino acid residue from the N-terminal of a variable region by the Kabat classification is deleted or substituted with an amino acid residue other than a proline residue;

(6a) a polypeptide having an amino acid sequence represented by SEQ ID NO: 6;

(6b) a polypeptide having an amino acid sequence which is obtained by substitution, addition, or deletion of one or more amino acids in the amino acid sequence represented by SEQ ID NO: 6 and in which the 95th amino acid residue from the N-terminal of a variable region by the Kabat classification is deleted or substituted with an amino acid residue other than a proline residue;

(6c) a polypeptide having an amino acid sequence which shares 90% or more identity with the amino acid sequence represented by SEQ ID NO: 6 and in which the 95th amino acid residue from the N-terminal of a variable region by the Kabat classification is deleted or substituted with an amino acid residue other than a proline residue;

(7a) a polypeptide having an amino acid sequence represented by SEQ ID NO: 7;

(7b) a polypeptide having an amino acid sequence which is obtained by substitution, addition, or deletion of one or more amino acids in the amino acid sequence represented by SEQ ID NO: 7 and in which the 95th amino acid residue from the N-terminal of a variable region by the Kabat classification is deleted or substituted with an amino acid residue other than a proline residue;

(7c) a polypeptide having an amino acid sequence which shares 90% or more identity with the amino acid sequence represented by SEQ ID NO: 7 and in which the 95th amino acid residue from the N-terminal of a variable region by the Kabat classification is deleted or substituted with an amino acid residue other than a proline residue.

The human κ light chain antibody having, as a variable region, a polypeptide having the amino acid sequence represented by SEQ ID NO:4 is also called "human κ light chain antibody (S34)" in some cases. In addition, the human κ light chain antibody having, as a variable region, a polypeptide having the amino acid sequence represented by SEQ ID NO:5 is also called "human κ light chain antibody (S38)" in some cases. The human κ light chain antibody (S34) and the human κ light chain antibody (S38) are proline deletants of the human κ light chain antibody (S35). In one embodiment, the full-length amino acid sequence of the human κ light chain antibody (S34) is represented by SEQ ID NO: 11, and the full-length amino acid sequence of the human κ light chain antibody (S38) is represented by SEQ ID NO: 12.

In the human κ light chain antibody (S34), CDR1 consists of the 24th to 39th amino acids in the amino acid sequences represented by SEQ ID NOs: 4 and 11, CDR2 consists of the 55th to 61st amino acids in the amino acid sequences represented by SEQ ID NOs: 4 and 11, and CDR3 consists of the 94th to 104th amino acids in the amino acid sequences represented by SEQ ID NOs: 4 and 11. In addition, the 219th cysteine in the amino acid sequence represented by SEQ ID NO: 11 is cysteine for forming a disulfide bond with other light chains.

In the human κ light chain antibody (S38), CDR1 consists of the 24th to 39th amino acids in the amino acid sequences represented by SEQ ID NOs: 5 and 12, CDR2 consists of the 55th to 61st amino acids in the amino acid sequences represented by SEQ ID NOs: 5 and 12, and CDR3 consists of the 94th to 103rd amino acids in the amino acid sequences represented by SEQ ID NOs: 5 and 12. In addition, the 218th cysteine in the amino acid sequence represented by SEQ ID NO: 12 is cysteine for forming a disulfide bond with other light chains.

The human κ light chain antibody (S34) and the human κ light chain antibody (S38) may be variants having a mutation that may not impair the enzyme activity. Particularly, as the human κ light chain antibody (S34) variant and the human κ light chain antibody (S34) variant, a variant having a mutation in a region other than a variable region is preferable, and a variant is more preferable in which CDR1, CDR2, and CDR3 are identical to (conserved as) the amino acid sequence represented by SEQ ID NO: 4, 5, 11, or 12 and amino acids other than the CDR regions in the variable region may be mutated from the human κ light chain antibody (S34) and the human κ light chain antibody (S38). Examples of the human κ light chain antibody (S34) variant include a human κ light chain antibody having the aforementioned polypeptide (4b) or (4c) as a variable region, and the like. Examples of the human κ light chain antibody (S38) variant include a human κ light chain antibody having the aforementioned polypeptide (5b) or (5c) as a variable region, and the like.

The human κ light chain antibody having, as a variable region, a polypeptide having the amino acid sequence represented by SEQ ID NO: 6 is also called "human κ light chain antibody (T99·P95Δ)" in some cases. The human κ light chain antibody (T99 P95Δ) is a proline deletant of the human κ light chain antibody (T99). In one embodiment, the full-length amino acid sequence of the human κ light chain antibody (T99 P95Δ) is represented by SEQ ID NO: 14. In the human κ light chain antibody (T99·P95Δ), CDR1 consists of the 24th to 39th amino acids in the amino acid sequences represented by SEQ ID NOs: 6 and 14, CDR2 consists of the 55th to 61st amino acids in the amino acid sequences represented by SEQ ID NOs: 6 and 14, and CDR3 consists of the 94th to 103rd amino acids in the amino acid sequences represented by SEQ ID NOs: 6 and 14. In addition, the 218th cysteine in the amino acid sequence represented by SEQ ID NO: 14 is cysteine for forming a disulfide bond with other light chains.

The human κ light chain antibody (T99·P95Δ) may be a variant having a mutation that may not impair the enzyme activity. Particularly, as the human κ light chain antibody (T99·P95Δ) variant, a variant having a mutation in a region other than a variable region is preferable, and a variant is more preferable in which CDR1, CDR2, and CDR3 are identical to (conserved as) the amino acid sequence represented by SEQ ID NO: 6 or 14 and amino acids other than the CDR regions in the variable region may be mutated from the human κ light chain antibody (T99·P95Δ). Examples of human κ light chain antibody (T99·P95Δ) variant include a human κ light chain antibody having the aforementioned polypeptide (6b) or (6c) as a variable region, and the like.

The human κ light chain antibody having, as a variable region, a polypeptide having the amino acid sequence represented by SEQ ID NO: 7 is also called "human κ light chain antibody (H34)" in some cases. The human κ light chain antibody (H34) is a proline deletant of the human κ light chain antibody (H55). In one embodiment, the full-length amino acid sequence of the human κ light chain antibody (H34) is represented by SEQ ID NO: 16. In the human κ light chain antibody (H34), CDR1 consists of the 24th to 39th amino acids in the amino acid sequences represented by SEQ ID NOs: 7 and 16, CDR2 consists of the 55th to 61st amino acids in the amino acid sequences represented by SEQ ID NOs: 7 and 16, and CDR3 consists of the 94th to 101st amino acids in the amino acid sequences represented by SEQ ID NOs: 7 and 16. In addition, the 213rd cysteine in the amino acid sequence represented by SEQ ID NO: 16 is cysteine for forming a disulfide bond with other light chains.

The human κ light chain antibody (H34) may be a variant having a mutation that may not impair the enzyme activity. Particularly, as the human κ light chain antibody (H34) variant, a variant having a mutation in a region other than a variable region is preferable, and a variant is more preferable in which CDR1, CDR2, and CDR3 are identical to (conserved as) the amino acid sequence represented by SEQ ID NO: 7 or 16 and amino acids other than the CDR regions in the variable region may be mutated from the human κ light chain antibody (H34). Examples of the human κ light chain antibody (H34) variant include a human κ light chain antibody having the aforementioned polypeptide (7b) or (7c) as a variable region, and the like.

Furthermore, the variable region of the κ light chain antibody (proline deletant) according to the present invention is preferably a polypeptide selected from the group consisting of the following (8a) to (8c).

(8a) An amino acid sequence obtained by deletion or substitution of the 100th proline residue from the N-terminal (95th proline residue from the N-terminal of a variable region by the Kabat classification) in an amino acid sequence represented by SEQ ID NO: 8;

(8b) a polypeptide having an amino acid sequence which is obtained by substitution, addition, or deletion of one or more amino acids in the amino acid sequence of the polypeptide (8a) and in which the 95th amino acid residue from the N-terminal of a variable region by the Kabat classification is deleted or substituted with an amino acid residue other than a proline residue;

(8c) a polypeptide having an amino acid sequence which shares 90% or more identity with the amino acid sequence of the polypeptide (8a) and in which the 95th amino acid residue from the N-terminal of a variable region by the Kabat classification is deleted or substituted with an amino acid residue other than a proline residue.

The mouse κ light chain antibody having, as a variable region, a polypeptide having the amino acid sequence represented by SEQ ID NO: 8 is also called "mouse κ light chain antibody (InfA-15L)" in some cases. The mouse κ light chain antibody (InfA-15L) can be obtained by adding a known human antibody constant region to the variable region described above. In one embodiment, the full-length amino acid sequence of InfA-15L is represented by SEQ ID NO: 17.

In the mouse κ light chain antibody (InfA-15L), CDR1 consists of the 21st to 39th amino acids in the amino acid sequences represented by SEQ ID NOs: 8 and 17, CDR2 consists of the 55th to 61st amino acids in the amino acid sequences represented by SEQ ID NOs: 8 and 17, and CDR3 consists of the 94th to 102nd amino acids in the amino acid sequences represented by SEQ ID NOs: 8 and 17. In addition, the 219th cysteine in the amino acid sequence represented by SEQ ID NO: 17 is cysteine for forming a disulfide bond with other light chains.

As will be shown in Examples later, the mouse κ light chain antibody (InfA-15L) does not have degradation activity on a substrate (hereinafter, called "trypsin-like pNA (R-pNA)" in some cases) consisting of benzoyl group (Bz group)-D-arginine/L-arginine-p-nitroaniline (pNA). However, the mouse κ light chain antibody including a variable region having an amino acid sequence which is obtained by deletion of substitution of the 95th proline residue from the N-terminal of a variable region by the Kabat classification in the amino acid sequence represented by SEQ ID NO: 8, that is, the mouse κ light chain antibody having the polypeptide (8a) as a variable region (hereinafter, called "proline deletant of the mouse κ light chain antibody (InfA-15L)" in some cases) can exhibit degradation activity on R-pNA. Therefore, the proline deletant of the mouse κ light chain antibody (InfA-15L) can be used as a trypsin-like enzyme. In order for the proline deletant of the mouse κ light chain antibody (InfA-15L) to exhibit trypsin-like enzyme activity, it is important for this protein to have a high ability to recognize a target molecule. Therefore, in the proline deletant of the mouse κ light chain antibody (InfA-15L), the variable region, particularly, the CDR sequence is the active center of the trypsin-like enzyme activity.

The proline deletant of the mouse κ light chain antibody (InfA-15L) may be a variant having a mutation that may not impair the enzyme activity. Particularly, as the variant of the proline deletant of the mouse κ light chain antibody (InfA-15L), a variant having a mutation in a region other than a variable region is preferable, and a variant is more preferable in which CDR1 and CDR2 are identical to (conserved as) the amino acid sequence represented by SEQ ID NO: 8 or 17, at least one of the 2nd and 3rd proline residues from the C-terminal of CDR3 is deleted or substituted but the amino acid sequence of CDR3 is identical (conversed) except for the proline residue, and amino acids other than the CDR regions in the variable region may be mutated from the mouse κ light chain antibody (InfA-15L). Examples of the variant of the proline deletant of the mouse κ light chain antibody (InfA-15L) include a mouse κ light chain antibody having the aforementioned polypeptide (8b) or (8c) as a variable region, and the like.

Examples of the variant of the proline deletant of the mouse κ light chain antibody (InfA-15L) include a polypeptide represented by an amino acid sequence obtained by deletion of the 95th proline residue and substitution of the 219th cysteine with alanine in the amino acid sequence represented by SEQ ID NO: 17, and the like.

The variable region of the κ light chain antibody (proline deletant) according to the present invention is also preferably a polypeptide selected from the group consisting of the following (9a) to (9c).

(9a) A polypeptide having an amino acid sequence represented by SEQ ID NO: 9;

(9b) a polypeptide having an amino acid sequence which is obtained by substitution, addition, or deletion of one or more amino acids in the amino acid sequence represented by SEQ ID NO: 9 and in which the 95th amino acid residue from the N-terminal of a variable region by the Kabat classification is deleted or substituted with an amino acid residue other than a proline residue;

(9c) a polypeptide having an amino acid sequence which shares 90% or more identity with the amino acid sequence represented by SEQ ID NO: 9 and in which the 95th amino acid residue by the Kabat classification from the N-terminal of the variable region is deleted or substituted with an amino acid residue other than a proline residue.

The mouse κ light chain antibody having, as a variable region, a polypeptide having the amino acid sequence represented by SEQ ID NO: 9 is also called "mouse κ light chain antibody (InfA-15L·P95Δ)" in some cases. The mouse κ light chain antibody (InfA-15L·P95Δ) is a proline deletant of the mouse κ light chain antibody (InfA-15L). In one embodiment, the full-length amino acid sequence of the mouse κ light chain antibody (InfA-15L·P95Δ) is represented by SEQ ID NO: 18. In the mouse κ light chain antibody (InfA-15L·P95Δ), CDR1 consists of the 21st to 39th amino acids in the amino acid sequences represented by SEQ ID NOs: 9 and 18, CDR2 consists of the 55th to 61st amino acids in the amino acid sequences represented by SEQ ID NOs: 9 and 18, and CDR3 consists of the 94th to 101st amino acids in the amino acid sequences represented by SEQ ID NOs: 9 and 18. In addition, the 218th cysteine in the amino acid sequence represented by SEQ ID NO: 18 is cysteine for forming a disulfide bond with other light chains.

The mouse κ light chain antibody (InfA-15L·P95Δ) may be a variant having a mutation that may not impair the enzyme activity. Particularly, as the mouse κ light chain antibody (InfA-15L·P95Δ) variant, a variant having a mutation in a region other than a variable region is preferable, and a variant is more preferable in which CDR1, CDR2, and CDR3 are identical to (conserved as) the amino acid sequence represented by SEQ ID NO: 9 or 18 and amino acids other than the CDR regions in the variable region may be mutated from the mouse κ light chain antibody (InfA-15L·P95Δ). Examples of mouse κ light chain antibody (InfA-15L·P95Δ) variant include a human κ light chain antibody having the aforementioned polypeptide (9b) or (9c) as a variable region, and the like.

The κ light chain antibody according to the present invention is not limited to those exemplified above. For example, for a known κ light chain antibody, by deleting or substituting the 95th proline residue from the N-terminal of a variable region by the Kabat classification, it is possible to cause the antibody to exhibit enzyme activity while maintaining the antigen recognition ability thereof.

The κ light chain antibody according to the present invention may contain an additional polypeptide. Examples of the additional polypeptide include epitope-labeled polypeptides such as a His tag, a Myc tag, and a Flag tag.

Those skilled in the related art can easily mutate one or more amino acids among amino acid residues constituting a polypeptide or can add an epitope-labeled polypeptide or the like by using a known technique. For example, by a known point mutation introduction method, any base of a polynucleotide encoding a polypeptide can be mutated. In addition, it is possible to prepare a deletion variant or an addition variant by designing a primer corresponding to any site of a polynucleotide encoding a polypeptide.

The κ light chain antibody according to the present invention includes a product of natural purification, a product of a chemical synthesis procedure, and a product obtained from prokaryotic or eukaryotic hosts (such as bacterial cells, yeast cells, higher plant cells, insect cells, and mammal cells) by a recombination technique. Depending on the host used in the recombination production procedure, the κ light chain antibody according to the present invention can be glycosylated or non-glycosylated. Furthermore, in some cases, the κ light chain antibody according to the present invention can contain a modified initiator methionine residue as a result of a host-mediated process.

The κ light chain antibody according to the present invention may be a polypeptide consisting of amino acids forming peptide bonds. However, the κ light chain antibody is not limited thereto, and may be a complex polypeptide including a structure other than a polypeptide. Examples of "structure other than a polypeptide" used in the present specification include a sugar chain, an isoprenoid group, and the like. However, the structure is not particularly limited.

<<Pharmaceutical Composition>>

The κ light chain antibody according to the present invention is particularly suitably used as a pharmaceutical composition such as an anticancer agent, an antiviral agent, or an amyloid β-degrading agent.

In order to be used for humans or animals, the anticancer agent according to the present invention (anticancer agent containing the κ light chain antibody according to the present invention as an active ingredient) can be administered by direct injection. Furthermore, the anticancer agent according to the present invention can be formulated for parenteral administration, mucosal administration, intramuscular administration, intravenous administration, subcutaneous administration, intraocular administration, or transdermal administration. Typically, the protein contained in the composition can be administered at a dose of 0.01 to 30 mg/kg body weight, preferably at a dose of 0.1 to 10 mg/kg body weight, and more preferably at a dose of 0.1 to 1 mg/kg body weight.

The anticancer agent according to the present invention can contain a pharmacologically acceptable carrier, diluent, or excipient (including a combination of these) in addition to the κ light chain antibody according to the present invention. Pharmacologically acceptable carriers or excipients for therapeutic use are well known in the pharmaceutical field. Such a carrier or excipient is described, for example, in Remington's Pharmaceutical Sciences, Mack Publishing Co. (edited by A. R. Gennaro, 1985). Those skilled in the art can easily select a pharmacologically usable carrier, excipient, or diluent depending on the intended route of administration and standard pharmaceutical practices. In addition, the anticancer agent according to the present invention can further contain any suitable binder, lubricant, suspending agent, coating agent, or solubilizing agent.

The composition/formulation requirements can vary with the delivery systems. For example, the anticancer agent according to the present invention can be formulated, for example, as a nasal spray or aerosol for inhalation using a minipump or mucosal route or formulated for parental delivery (herein, the anticancer agent according to the present invention is formulated as an injectable agent for delivery through, for example, an intravenous route, an intramuscular route, or a subcutaneous route). Alternatively, the formulation can be designed to be delivered through both routes. In addition, a formulation, such as a nasal spray or aerosol for inhalation, which can be efficiently delivered to lung cells from the nose, bronchi, and the like is also preferable.

In a case where the anticancer agent according to the present invention is to be used for in vivo administration, it is possible to use various techniques for improving in vivo stability (half-life in blood) of the κ light chain antibody which is an active ingredient. For instance, it is known that the binding of neonatal Fc receptor (FcRn) to Fc extends the half-life of antibodies such as IgG in blood (for example, see Roopenian, D. C. et. al., Nat Rev Immunol vol. 7. 715-725 (2007)). The κ light chain antibody according to the present invention can be modified so that the C-terminal thereof has FcRn-binding activity. Furthermore, it is also possible to dimerize the κ light chain antibody according to the present invention or to add PEG (polyethylene glycol) thereto.

The anticancer agent according to the present invention can also be made into a kit including instructions on the mode of administration or the like. The kit can also include various medicines that can be used in combination with the anticancer agent according to the present invention.

The anticancer agent according to the present invention contains, as an active ingredient, the κ light chain antibody having a high ability to recognize a target molecule. Therefore, the anticancer agent does not exhibit cytotoxicity to cancer cells in which the target molecule of the κ light chain antibody does not exist on the cell surface. Accordingly, the anticancer agent of the present invention is expected to be useful for identifying the type of cancer.

EXAMPLES

Hereinafter, the present invention will be more specifically described with reference to Examples, but the present invention is not limited to these examples.

[Construction of Expression System for Human κ Light Chain Antibody]

In the following examples and the like, the human κ light chain antibody (S35) having the amino acid sequence represented by SEQ ID NO: 10, the human κ light chain antibody (T99) having the amino acid sequence represented by SEQ ID NO: 13, the human κ light chain antibody (H55) having the amino acid sequence represented by SEQ ID NO: 15, the human κ light chain antibody (S34) having the amino acid sequence represented by SEQ ID NO: 11, the human κ light chain antibody (S38) having the amino acid sequence represented by SEQ ID NO: 12, the human κ light chain antibody (T99·P95Δ) having the amino acid sequence represented by SEQ ID NO: 14, the human κ light chain antibody (H34) having the amino acid sequence represented by SEQ ID NO: 16, the mouse κ light chain antibody (InfA-15L) having the amino acid sequence represented by SEQ ID NO: 17, the mouse κ light chain antibody (InfA-15L·P95Δ) having the amino acid sequence represented by SEQ ID NO: 18, and the human κ light chain antibody (#7 wt) having the amino acid sequence represented by SEQ ID NO: 19 were used. These human κ light chain antibodies are banked human κ light chain antibodies produced from B lymphocytes.

Each of these human κ light chain antibodies was expressed in an *E. coli* expression system. Specifically, cDNA having a base sequence encoding each of the human κ light chain antibodies was introduced into a plasmid vector having a His tag sequence site, and the plasmid vector was introduced into *E. coli*, thereby preparing a transformant. Each transformant was cultured, expression thereof was induced by IPTG, and the protein was subjected to SDS-PAGE analysis and Western blotting using an anti-human (Fab') 2 antibody. As a result, the protein expressed in *E. coli* was identified as a human light chain antibody. The obtained human light chain antibody had M (methionine) at the N-terminal and LEHHHHHH (SEQ ID NO: 20) derived from the plasmid vector at the C-terminal.

[Expression and Purification of Human κ Light Chain Antibody]

The human κ light chain antibody not being treated with metal ions and not being subjected to metal ion removal was expressed and purified as below.

First, the *E. coli* transformant transfected with the expression vector prepared as above was cultured at 37° C. overnight in LB medium, then IPTG was added to the culture medium so that the final concentration thereof became 10 μM (μmol/L), and the cell was cultured at 18° C. overnight. After culturing, the culture was centrifuged, and the cells collected from the culture were added to sodium chloride-containing Tris buffer (25 mM Tris-HCl, 0.25M NaCl, pH 8.0) and treated with ultrasonic waves, thereby inducing cell lysis. Then, the cell lysate was centrifuged, and a soluble fraction was recovered.

Thereafter, as a first purification step, the soluble fraction was applied to Ni-NTA column (manufactured by QIAGEN) filled with Ni-NTA agarose, and an appropriate amount of the sodium chloride-containing Tris buffer was passed through the Ni-NTA column so that the expressed human κ light chain antibody was adsorbed onto the Ni-NTA column. Subsequently, by using an imidazole-containing Tris buffer (25 mM Tris-HCl, 0.25 M NaCl, imidazole, pH 8.0) having an imidazole concentration gradient of 0.03 M to 0.3 M as an eluent, the human κ light chain antibody was eluted from the Ni-NTA column, and a human κ light chain antibody-containing fraction was isolated. The recovered human κ light chain antibody-containing fraction was dialyzed with an acetate buffer (50 mM acetate, pH 5.5) at 4° C. for 12 to 24 hours.

Then, as a second purification step, the dialyzed human κ light chain antibody-containing fraction was applied to a cation exchange column (product number: SP-5PW, manufactured by TOSOH CORPORATION), and an appropriate amount of the acetate buffer was passed through the cation exchange column so that the expressed human κ light chain antibody was adsorbed onto the cation exchange column. Thereafter, by using, as an eluent, a sodium chloride-containing acetate buffer (50 mM acetate, NaCl, pH 5.5) having a sodium chloride concentration gradient of 0.15 M to 0.45 M or a sodium chloride-containing Tris-HCl buffer (pH 8.0) having a sodium chloride concentration gradient of 0.0 w/v % to 15.0 w/v %, the human κ light chain antibody was eluted from the cation exchange column, and a human κ light chain antibody-containing fraction was isolated. Alternatively, purification was performed using size exclusion chromatography (column; HiLoad™ 16/60 Superdex™ 200 pg (GE healthcare)) instead of the cation exchange column and using PBS (pH=7.4) as an elution solvent.

The recovered human κ light chain antibody-containing fraction was dialyzed with a sodium chloride-containing Tris buffer (20 mM Tris-HCl, 0.15 M NaCl, pH 8.5) at 4° C. for 12 to 24 hours, and then further dialyzed with PBS (pH 7.4) at 4° C. for 12 to 24 hours. The resultant obtained after dialysis was used as a human κ light chain antibody.

[Evaluation of Enzyme Activity]

By using an evaluation system that uses FRET peptide represented by the following structural formula as a substrate, the enzyme activity of each human κ light chain antibody was evaluated. In the structural formula, "MCA" represents a 7-methoxycoumarin-4-methylamide structure, and "DNP" represents a 2,4-dinitrophenyl group. "Lys" represents a lysine residue, and "D-Arg" represents a D-arginine residue.

MCA-(antigen peptide)-Lys(DNP)-(D-Arg)$_3$

The types and sequences of antigen peptides are shown in the following Table 1. In Table 1, "Aβ" represents amyloid β and "Tau" represents tau protein, both of which are dementia-inducing substances. "PD-1" is an immune checkpoint molecule. The numbers in the brackets show the position from the N-terminal in the full-length amino acid sequence, for which a partial peptide was used. In addition, "pS" in the amino acid sequence of the tau protein means a phosphorylated serine residue.

TABLE 1

| | Amino acid sequence | SEQ ID NO: |
|---|---|---|
| Aβ (26-33) | 5'-SNKGAIIG-3' | 21 |
| Tau (391-408) | 5'-EIVYKpSPVVSGDTpSPRHL-3' | 22 |
| PD-1 (124-141) | 5'-GAISLAPKAQIKESLRAE-3' | 23 |

The human κ light chain antibody and the FRET substrate were added to 100 μL of PBS (pH 7.4) so that the final concentration of the antibody and substrate became 5 μM and 100 μM respectively, the solution was incubated at 37° C. for up to 120 hours, and a temporal change in p-nitroaniline (main wavelength 405 nm, sub-wavelength 620 nm) concentration caused by substrate cleavage was measured.

Example 1

By using the human κ light chain antibody (#7 wt), how the copper ion addition and the subsequent copper ion removal in the purification step affect the storage stability of the human κ light chain antibody was investigated.

Specifically, the human κ light chain antibody (#7 wt) was prepared by the same method as in [Expression and purification of human κ light chain antibody] described above (Case 1), except that as described in [Expression and purification of human κ light chain antibody], in the method of expressing and purifying the antibody in the absence of copper ions (control case), copper ions were added to the eluate obtained after the Ni-NTA column purification so that the final concentration became 15 μM, the solution was then incubated for 12 to 16 hours at 4° C., then dialyzed with the aforementioned acetate buffer, and then purified using a cation exchange column, and the obtained eluate was then dialyzed with the aforementioned sodium chloride-containing Tris buffer to which ethylenediaminetetraacetic acid (EDTA) was added to yield a final concentration of 50 mM and then dialyzed with the aforementioned PBS. The obtained human κ light chain antibody (#7 wt) was stored at 4° C. for 3 months.

Comparative Example 1

The human κ light chain antibody (#7 wt) was prepared by the same method as in [Expression and purification of human κ light chain antibody] described above (Case 2), except that as described in [Expression and purification of human κ light chain antibody], in the method of expressing and purifying the antibody in the absence of copper ions (control case), copper ions were added to the eluate obtained after the Ni-NTA column purification so that the final concentration became 15 μM, and the solution was incubated for 12 to 16 hours at 4° C. and then dialyzed with the aforementioned acetate buffer. The obtained human κ light chain antibody (#7 wt) was stored at 4° C. for 3 days or 3 months.

Figure 1B:
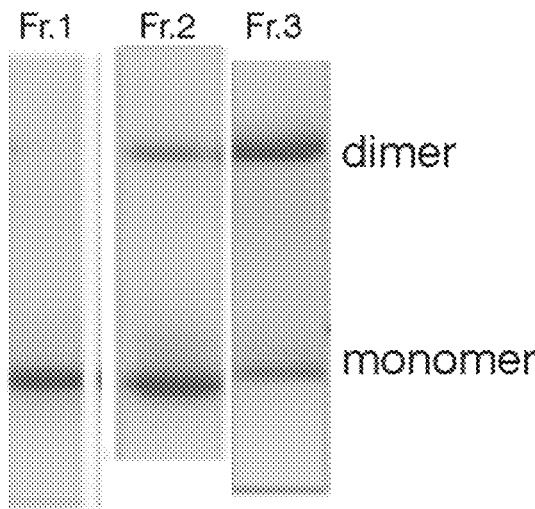
FIG. 1B is a diagram showing the results of SDS-PAGE (non-reducing) on each peak of the cation exchange chromatogram shown in FIG. 1A.

FIG. 1A shows a cation exchange chromatogram in the control case (without copper ions added) (UV (280 nm) absorbance (mAU) of the eluate and sodium chloride concentration (M) in the eluent at each retention time). FIG. 1B shows the results of SDS-PAGE (non-reducing) on fractions 1 to 3 shown in FIG. 1A. The fraction 1 contained only the monomer of the human κ light chain antibody (#7 wt). Although the fraction 2 contained both the monomer and dimer, the monomer content was higher. The fraction 3 mainly contained a dimer.

Figure 2A:
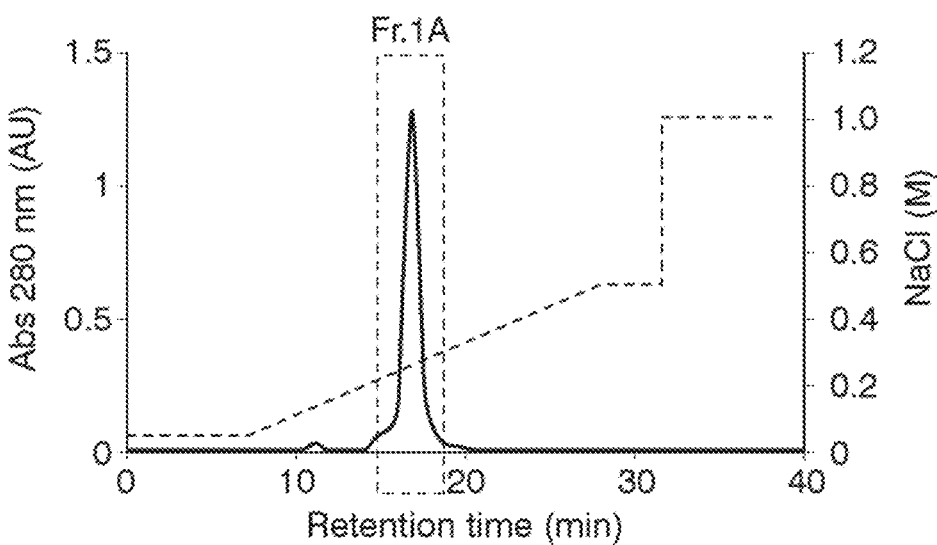
FIG. 2A is a cation exchange chromatogram in Case 1 (addition of copper ions after primary purification and removal of copper ions after secondary purification) in Example 1.
Figure 2B:
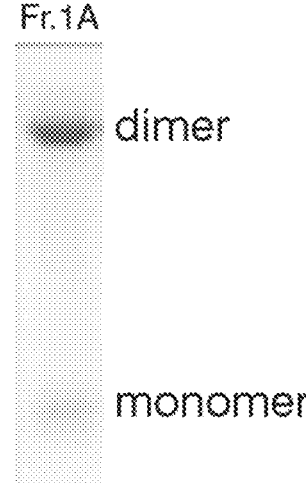
FIG. 2B is a diagram showing the results of SDS-PAGE (non-reducing) on peaks of the cation exchange chromatogram shown in FIG. 2A.
Figure 2C:
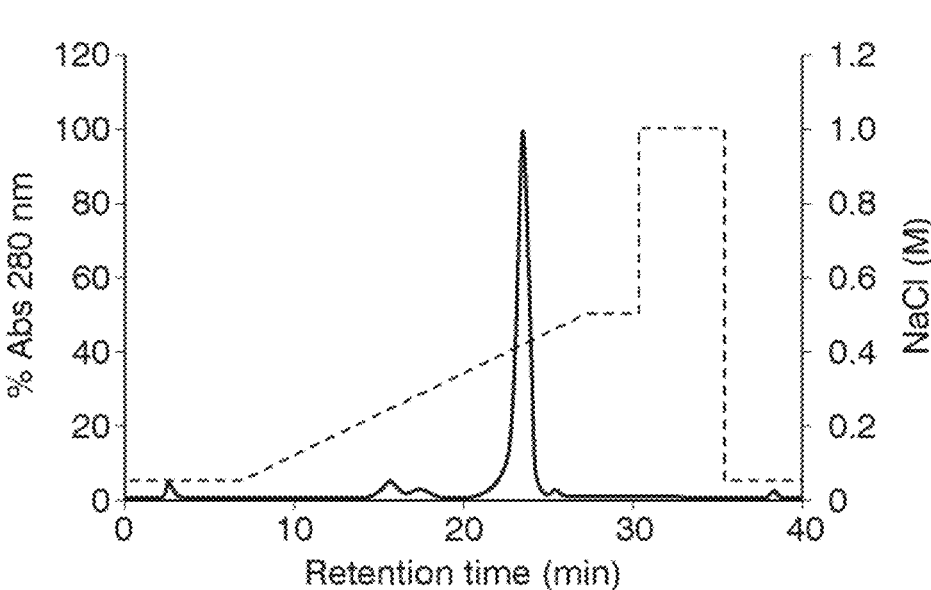
FIG. 2C is a cation exchange chromatogram obtained after a human κ light chain antibody purified in Case 1 (addition of copper ions after primary purification and removal of copper ions after secondary purification) in Example 1 is stored at 4° C. for 3 months.

FIG. 2A shows the cation exchange chromatogram in Case 1 (copper ion addition after primary purification and copper ion removal after secondary purification). FIG. 2B shows the results of SDS-PAGE (non-reducing) on the fraction 1A shown in FIG. 2A. FIG. 2C shows the cation exchange chromatogram in Case 1 after storage at 4° C. for 3 months. In Case 1, one large peak was observed at a position corresponding to the fraction 3 of the control case. The results of SDS-PAGE indicate that the human κ light chain antibody (#7 wt) contained in the fraction 1A is substantially a dimer, and a dimer is more easily formed than a monomer by the purification in the presence of copper ions. Furthermore, even after the storage at 4° C. for 3 months, one large peak was still observed at a position corresponding to the fraction 3 of the control case. This result indicates that the removal of copper ions makes it possible to stably store the antibody for a long period of time.

Figure 3A:
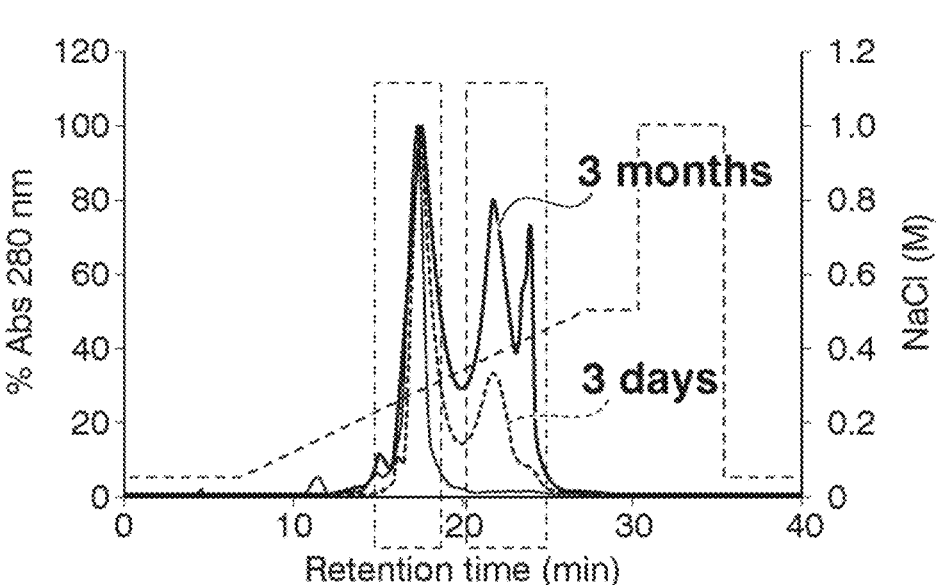
FIG. 3A is a cation exchange chromatogram of a human κ light chain antibody that is obtained immediately after purification in Case 2 (addition of copper ions after primary purification), after storage at 4° C. for 3 months, and after storage for 3 months in Comparative Example 1.
Figure 3B:
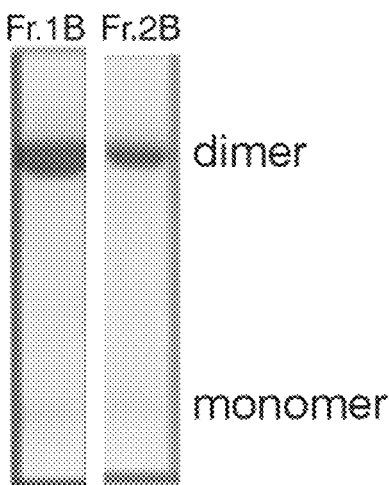
FIG. 3B is a diagram showing the results of SDS-PAGE (non-reducing) on each peak of the human κ light chain antibody after the storage at 4° C. for 3 months in the cation exchange chromatogram shown in FIG. 3A.

FIG. 3A shows the cation exchange chromatogram in Case 2 (copper ion addition after primary purification), and FIG. 3B shows the results of SDS-PAGE (non-reducing) on the fractions 1B and 2B shown in FIG. 3A. In Case 2, immediately after purification, one large peak was observed at a position corresponding to the fraction 3 of the control case. However, during the storage for 3 days or 3 months at 4° C., the number of peaks tended to increase with the passage of time. The increased peaks also resulted from the dimer, which leads to the inference that the presence of copper ions made the structure of a part of the dimer unstable.

Example 2

By using the human κ light chain antibody (S35), the human κ light chain antibody (S34), and the human κ light chain antibody (S38), the degradation activity on the Aβ peptide was evaluated.

Specifically, the human κ light chain antibody (S35), the human κ light chain antibody (S34), and the human κ light chain antibody (S38) were obtained using the same method as that in Case 1 of Example 1. Then, the degradation activity of each of the human κ light chain antibodies on the Aβ peptide was evaluated by the same method as that in [Evaluation of enzyme activity] described above, except that the concentration of the FRET substrate was set to 25 μM.

Figure 4A:
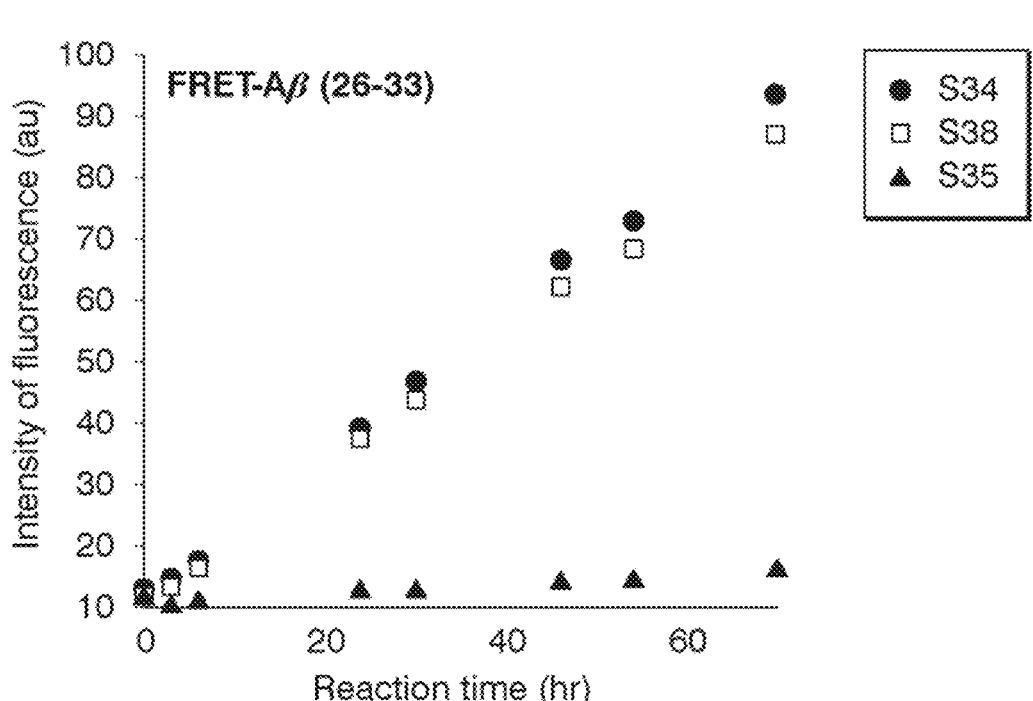
FIG. 4A is a graph showing the temporal change of FRET-Aβ peptide degradation activity of a human κ light chain antibody (S35), a human κ light chain antibody (S34), and a human κ light chain antibody (S38) in Example 2.

FIG. 4A is a graph showing the temporal change of FRET-A0 peptide degradation activity of the human κ light chain antibody (S35), the human κ light chain antibody (S34), and the human κ light chain antibody (S38). The human κ light chain antibody (S34) and the human κ light chain antibody (S38) increased fluorescence intensity with the passage of time, which shows that these antibodies have Aβ peptide degradation activity. In contrast, substantially no fluorescence was detected from the sample treated with the human κ light chain antibody (S35), which shows that this antibody does not have Aβ peptide degradation activity.

Figure 4B:
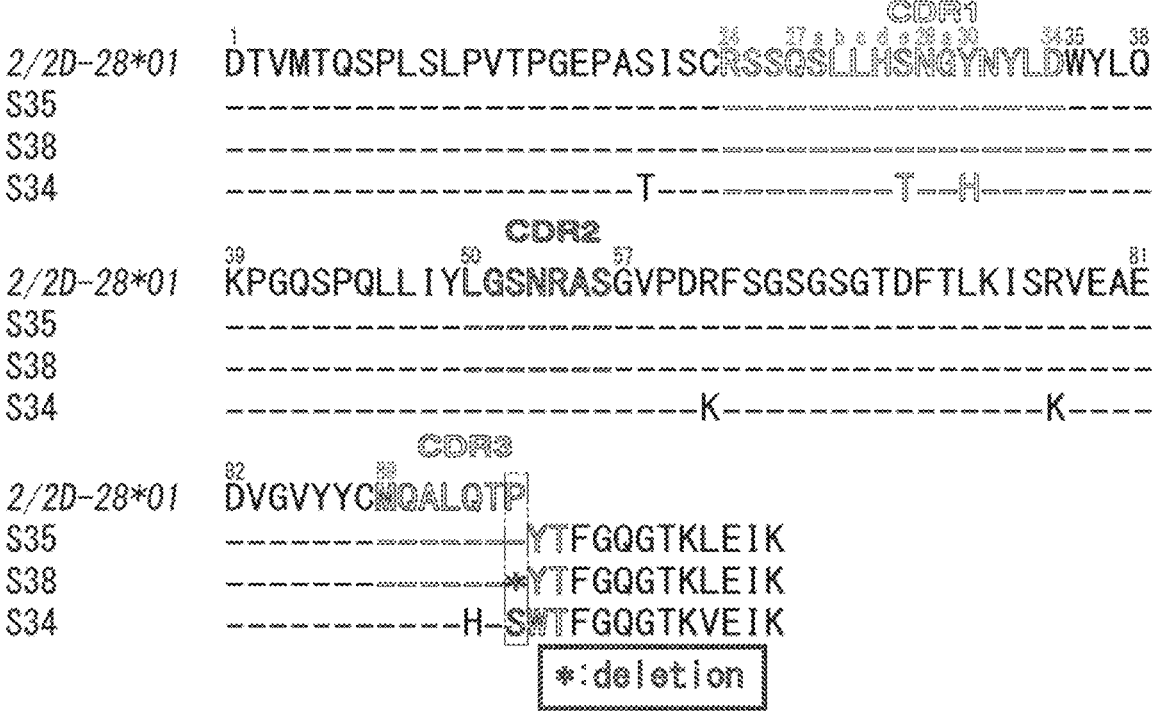
FIG. 4B shows amino acid sequences of variable regions of the human κ light chain antibody (S35), the human κ light chain antibody (S34), and the human κ light chain antibody (S38) in Example 2.

FIG. 4B shows amino acid sequences of variable regions of the human κ light chain antibody (S35), the human κ light chain antibody (S34), and the human κ light chain antibody (S38). In FIG. 4B, 2/2D-28*01 is one of the light chains encoded by the V gene of subgroup II present on the fertilized egg chromosome. FIG. 4B shows the amino acid sequence (SEQ ID NO: 24) of the portion corresponding to the variable region of the human κ light chain antibody (S35), the human κ light chain antibody (S34), and the human κ light chain antibody (S38). In addition, "-" means the same amino acid residue as that in 2/2D-28*01. By the comparison of amino acid sequences, it was confirmed that while the human κ light chain antibody (S35) has a proline residue at the 95th position from the N-terminal of a variable region by the Kabat classification, the human κ light chain antibody (S38) has deletion of the proline residue, and the human κ light chain antibody (S34) has a serine residue substituting for the proline residue. Presumably, the deletion or substitution of the proline residue may markedly improve the activity of the antibody-enzyme.

Example 3

How the presence or absence of the 95th proline residue from the N-terminal of a variable region by the Kabat classification in the amino acid sequence of the variable region affects the activity of antibody-enzyme was investigated. That is, the Aβ peptide degradation activity was evaluated using the human κ light chain antibody (T99), which is a clone having the 95th proline residue from the N-terminal of a variable region by the Kabat classification in the amino acid sequence of the variable region, and the human κ light chain antibody (T99·P95Δ), which is obtained by deleting the 95th proline residue from the N-terminal of a variable region by the Kabat classification in the amino acid sequence of the variable region of the human κ light chain antibody (T99).

Specifically, the human κ light chain antibody (T99) and the human κ light chain antibody (T99·P95Δ) were obtained using the same method as that in Case 1 of Example 1. Then, the degradation activity of each of the human κ light chain antibodies on the Aβ peptide was evaluated by the same method as that in [Evaluation of enzyme activity] described above.

Figure 5A:
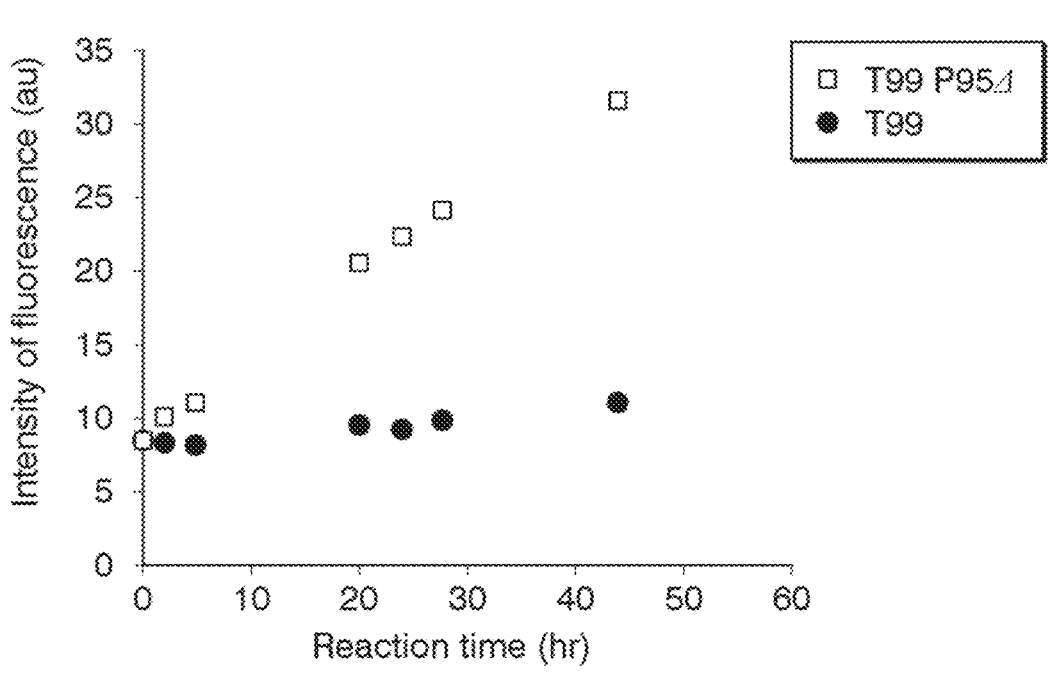
FIG. 5A is a graph showing the temporal change of FRET-Aβ peptide degradation activity of a human κ light chain antibody (T99) and a human κ light chain antibody (T99·P95Δ) in Example 3.

FIG. 5A is a graph showing the temporal change of FRET-Aβ peptide degradation activity of the human κ light chain antibody (T99) and the human κ light chain antibody (T99·P95Δ). The human κ light chain antibody (T99·P95Δ) increased fluorescence intensity with the passage of time, which shows that this antibody has Aβ peptide degradation activity. In contrast, substantially no fluorescence was detected from the sample treated with the human κ light chain antibody (T99), which shows that this antibody does not have Aβ peptide degradation activity.

Figure 5B:
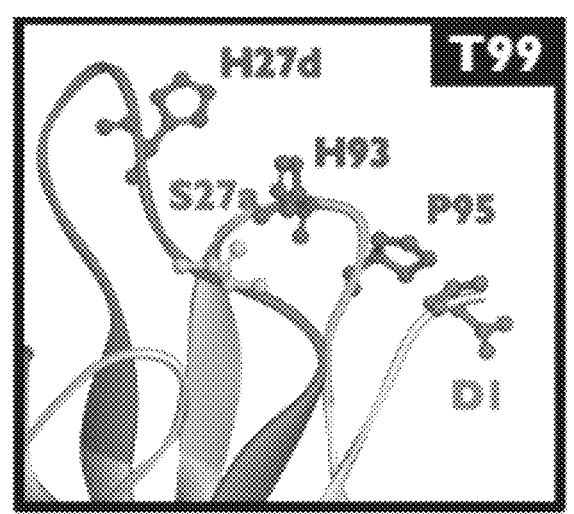
FIG. 5B shows diagrams of predicted three-dimensional structures of the variable regions of the human κ light chain antibody (T99) and the human κ light chain antibody (T99 P95Δ) in Example 3.
Figure 5B:
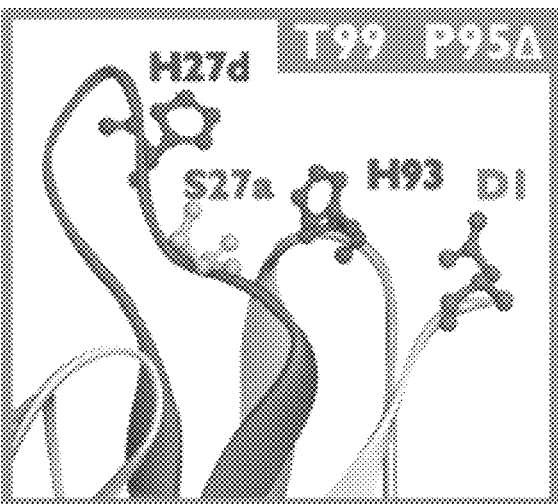

FIG. 5B shows diagrams of predicted three-dimensional structures of the variable regions of the human κ light chain antibody (T99) and the human κ light chain antibody (T99 P95Δ). In FIG. 5B, "527a" represents the 27th serine residue from the N-terminal of a variable region by the Kabat classification, "H27d" represents the 27th histidine residue from the N-terminal of a variable region by the Kabat classification, "H93" represents the 93rd histidine residue from the N-terminal of a variable region by the Kabat classification, "P95" represents the 95th proline residue from the N-terminal of a variable region by the Kabat classification, and "D1" represents the 1st aspartic acid from the N-terminal of a variable region by the Kabat classification. It was revealed that the deletion of the 95th proline residue from the N-terminal of a variable region by the Kabat classification in the amino acid sequence of the variable region significantly changes the distance between amino acid residues (distance between H93 and D1 in FIG. 5B) constituting the enzyme activity site (catalytic triad-like structure).

It was confirmed that the human κ light chain antibody (S35) also has the catalytic triad-like structure shown in FIG. 5B just as the human κ light chain antibody (T99). Presumably, this indicates that many Vk genes of subgroup II have the catalytic triad-like structure, but not all the κ light chains prepared from such genes have enzyme activity. However, by deleting the 95th proline residue from the N-terminal of a variable region by the Kabat classification in the amino acid sequence of the variable region or substituting such a residue with an amino acid residue having a more compact structure compared to the proline residue, it is possible to appropriately change the arrangement of the catalytic triad-like structure, which implies that peptidase activity could be imparted to the antibody.

Example 4

For clones derived from the Vκ gene of subgroup I, how the presence or absence of the 95th proline residue from the N-terminal of a variable region by the Kabat classification in the amino acid sequence of the variable region affects the activity of the antibody-enzyme was investigated. That is, the PD-1 peptide degradation activity was evaluated using the human κ light chain antibody (h55), which is a clone having the 95th proline residue from the N-terminal of a variable region by the Kabat classification in the amino acid sequence of the variable region, and the human κ light chain antibody (H34), which does not have the 95th proline residue from the N-terminal of a variable region by the Kabat classification in the amino acid sequence of the variable region.

Specifically, the human κ light chain antibody (H55) and the human κ light chain antibody (H34) were obtained using the same method as that in Case 1 of Example 1. Then, the degradation activity of each of the human κ light chain antibodies on the PD-1 peptide was evaluated by the same method as that in [Evaluation of enzyme activity] described above.

Figure 6A:
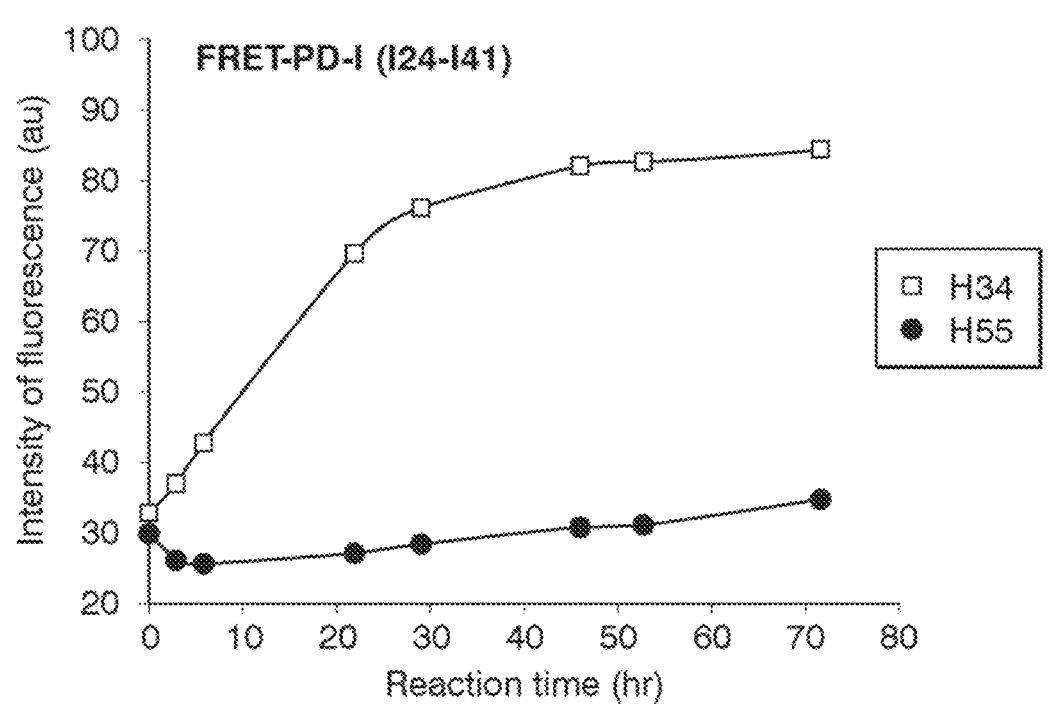
FIG. 6A is a graph showing the temporal change of FRET-PD-1 peptide degradation activity of a human κ light chain antibody (H55) and a human κ light chain antibody (H34) in Example 3.

FIG. 6A is a graph showing the temporal change of FRET-PD-1 peptide degradation activity of the human κ light chain antibody (H55) and the human κ light chain antibody (H34). The human κ light chain antibody (H34) increased fluorescence intensity with the passage of time, which shows that this antibody has PD-1 peptide degradation activity. In contrast, substantially no fluorescence was detected from the sample treated with the human κ light chain antibody (H55), which shows that this antibody does not have PD-1 peptide degradation activity.

Figures 6B, 6C:
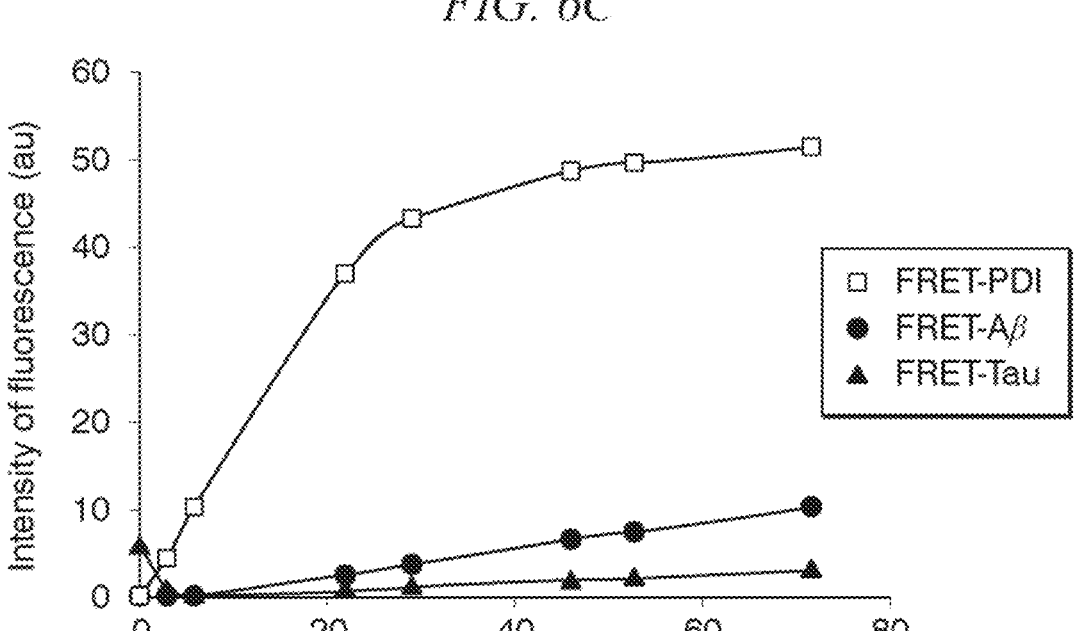
FIG. 6B shows amino acid sequences of the variable regions of the human κ light chain antibody (H55) and the human κ light chain antibody (H34) in Example 3.
FIG. 6C is a graph showing the temporal change of degradation activity of the human κ light chain antibody (H34) on FRET-Aβ peptide, FRET-Tau peptide, and FRET-PD-1 peptide in Example 3.

FIG. 6B shows amino acid sequences of the variable regions of the human κ light chain antibody (H55) and the human κ light chain antibody (H34). In FIG. 6B, each of 1-39*01 and 1-5*03 is one of the light chains encoded by the V gene of subgroup I present on the fertilized egg chromosome. FIG. 6B shows the amino acid sequences (SEQ ID NOs: 25 and 26) of the portions corresponding to the variable regions of the human κ light chain antibody (H55) and the human κ light chain antibody (H34) respectively. "-" means the same amino acid residue as that in 1-39*01 for the human κ light chain antibody (H55), and means the same amino acid residue as that in 1-5*03 for the human κ light chain antibody (H34). By the comparison of amino acid sequences, it was confirmed that while the human κ light chain antibody (H55) has a proline residue at the 95th position from the N-terminal of a variable region by the Kabat classification, the human κ light chain antibody (H34) has an arginine residue substituting for the proline residue. Presumably, this result indicates that the deletion or substitution of the proline residue may also markedly improve the activity of the antibody-enzyme for the clones derived from the Vκ gene of subgroup I.

In order to examine the substrate specificity of the human κ light chain antibody (H34), the degradation activity on the Aβ peptide, Tau peptide, and PD-1 peptide was evaluated using the same method as that in [Evaluation of enzyme activity] described above.

FIG. 6C is a graph showing the temporal change of degradation activity of the human κ light chain antibody (H34) on FRET-Aβ peptide, FRET-Tau peptide, and FRET-PD-1 peptide. It was confirmed that the human κ light chain antibody (H34) has degradation activity on the PD-1 peptide, but does not have degradation activity on the FRET-Aβ peptide and the FRET-Tau peptide. Therefore, it was revealed that the human κ light chain antibody (H34) specifically recognizes and degrades the PD-1 peptide.

In order to identify the degradation site of the PD-1 peptide by the human κ light chain antibody (H34), the solution obtained after the degradation test described above was analyzed by high-performance liquid chromatography (HPLC), and the peaks that appeared were collected and analyzed by mass spectrometry (MS). Each measurement condition will be shown below.

(HPLC Condition)

Device: Waters Delta 600, Waters 2489 UV/Visible Detector (manufactured by Waters Corporation.)

Column: Cosmosil type, 5C18-AR-2 (4.6×250 mm), Nacalai

Mobile phase: A phase (MilliQ water in 0.05% TFA), B phase (Acetonitrile in 0.05% TFA)

Gradient: 90% A phase to 40% A phase in 50 min (1%/min)

Flow rate: 1.0 mL/min

Detection: 220 nm (MS Condition)

Device: microTOF-Q (manufactured by Bruker Daltonics Inc.)

Figure 6D:
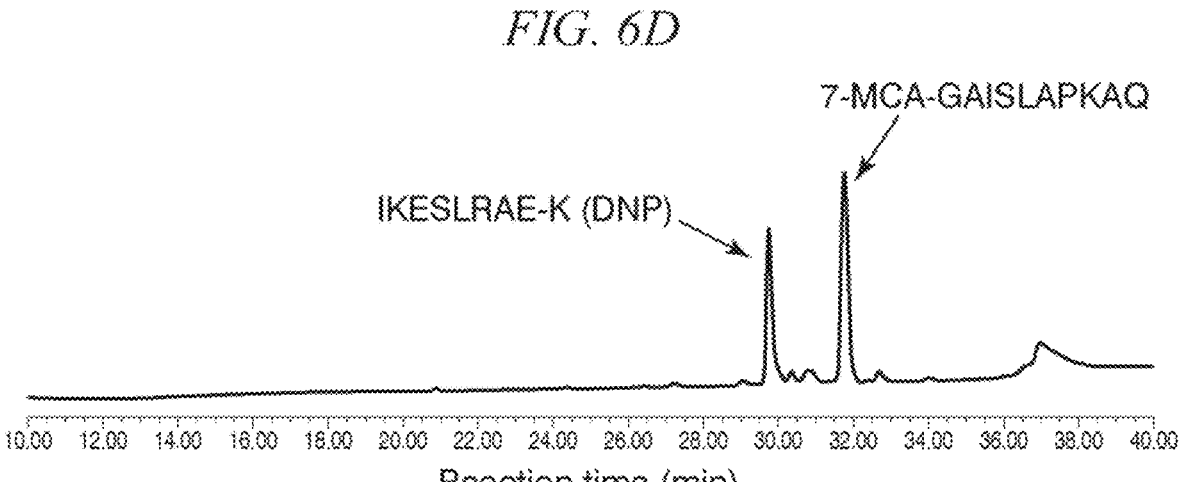
FIG. 6D is a high-performance liquid chromatogram of a solution obtained after a PD-1 peptide degradation test on the human κ light chain antibody (H34) in Example 3.

FIG. 6D is a high-performance liquid chromatogram of a solution obtained after a PD-1 peptide degradation test on the human κ light chain antibody (H34). It was revealed that the degradation site of the PD-1 peptide is a peptide bond between Q (glutamine) and I (isoleucine).

Furthermore, the degradation activity of the human κ light chain antibody (H34) on the full-length recombinant human PD-1 was evaluated. Specifically, the degradation activity was evaluated by the same method as that in [Evaluation of enzyme activity] described above, except that the full-length recombinant human PD-1 was used as a substrate, and human serum albumin (HSA) was used as a control substrate.

Figure 6E:
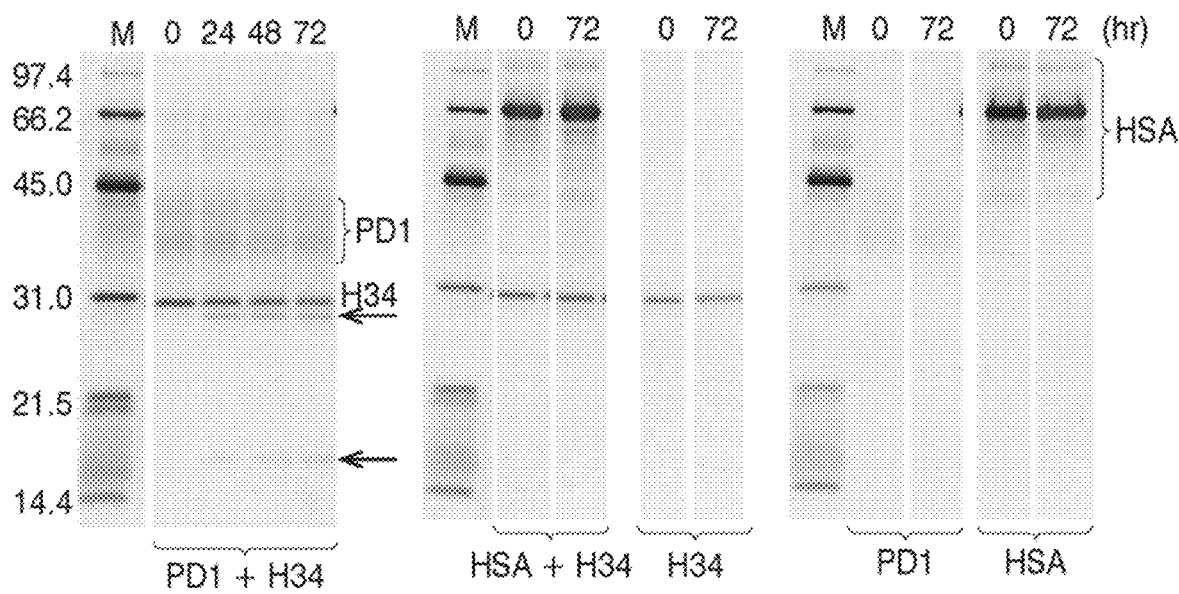
FIG. 6E shows diagrams of the results of SDS-PAGE (non-reducing) on each solution obtained after recombinant human PD-1 and human serum albumin (HSA) degradation tests in Example 3.

FIG. 6E shows the results of SDS-PAGE (non-reducing) on each solution obtained after the degradation test. Degraded PD-1 fragments were found at the portion indicated by arrows, which shows that the human κ light chain antibody (H34) has degradation activity on the full-length recombinant human PD-1.

Furthermore, in order to evaluate how the presence or absence of the 95th proline residue from the N-terminal of a variable region by the Kabat classification affects the enzyme activity of the human κ light chain antibody (H34), a variant (hereinafter, called "human κ light chain antibody (H34_P95(+))" in some cases) (SEQ ID NO: 27) was prepared which was obtained by inserting a proline residue into the 95th position from the N-terminal of a variable region by the Kabat classification of the human κ light chain antibody (H34).

Specifically, the human κ light chain antibody (H34) and the human κ light chain antibody (H34_P95(+)) were obtained using the same method as that in Case 1 of Example 1. Then, the degradation activity of each of the human κ light chain antibodies on the PD-1 peptide was evaluated by the same method as that in [Evaluation of enzyme activity] described above.

Figure 6F:
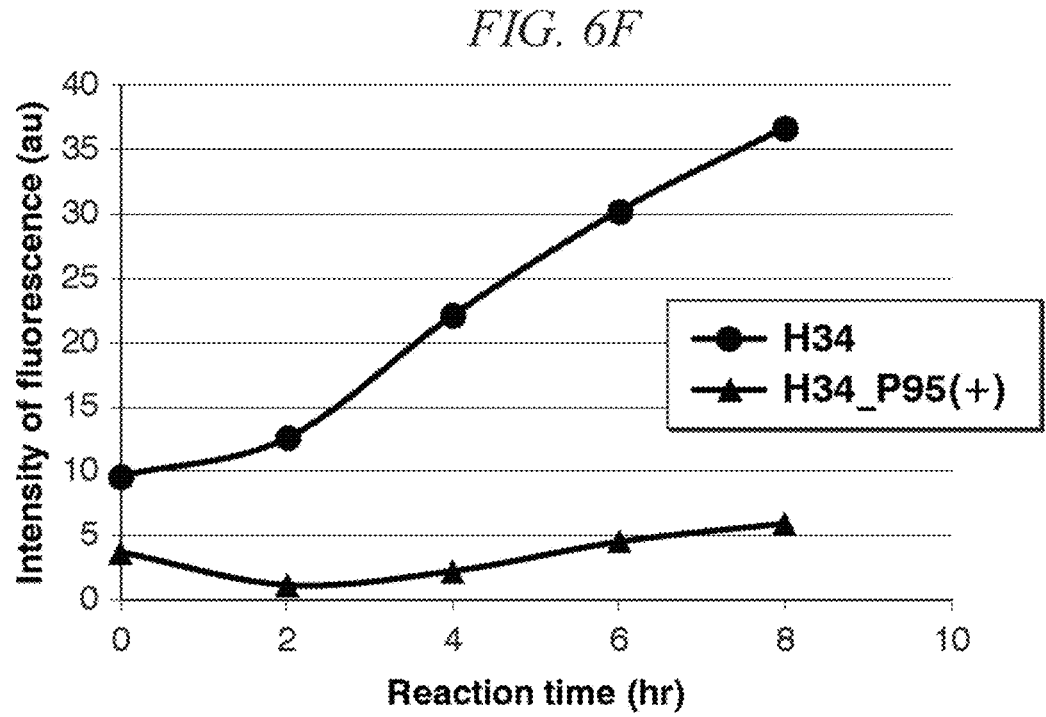
FIG. 6F is a graph showing the temporal change of FRET-PD-1 peptide degradation activity of a human κ light chain antibody (H34) and a human κ light chain antibody (H34_P95(+)) in Example 3.

FIG. 6F is a graph showing the temporal change of FRET-PD-1 peptide degradation activity of the human κ light chain antibody (H34) and the human κ light chain antibody (H34_P95(+)). The human κ light chain antibody (H34) increased fluorescence intensity with the passage of time, which shows that this antibody has PD-1 peptide degradation activity. In contrast, substantially no fluorescence was detected from the sample treated with the human κ light chain antibody (H34_P95(+)), which shows that this antibody does not have PD-1 peptide degradation activity. Therefore, it was confirmed that the activity of an antibody-enzyme changes depending on the presence or absence of the 95th proline residue from the N-terminal of a variable region by the Kabat classification.

The above results imply that the deletion or substitution of the 95th proline residue from the N-terminal of a variable region by the Kabat classification in the amino acid sequence of the variable region could bring about not only the enzyme activity of the κ light chain antibody derived from the Vk gene of subgroup II but also the enzyme activity of the κ light chain antibody derived from the Vk gene of other subgroups.

Example 5

For clones derived from the mouse Vκ gene, how the presence or absence of the 95th proline residue from the N-terminal of a variable region by the Kabat classification in the amino acid sequence of the variable region affects the activity of the antibody-enzyme was investigated. That is, the degradation activity on the trypsin-like p-nitroaniline (R-pNA) was evaluated using the mouse κ light chain antibody (InfA-15L), which is a clone having the 95th proline residue from the N-terminal of a variable region by the Kabat classification in the amino acid sequence of the variable region, and the mouse κ light chain antibody (InfA-15L·P95Δ), which is obtained by deleting the 95th proline residue from the N-terminal of a variable region by the Kabat classification from the amino acid sequence of the variable region. R-pNA is a substrate having the following structure. In a case where the peptide bond between arginine and pNA is hydrolyzed, pNA is dissociated, and fluorescence is detected.

R-pNA: Benzoyl Group (Bz Group)-D-Arginine/L-Arginine-pNA

Specifically, the mouse κ light chain antibody (InfA-15L) and the mouse κ light chain antibody (InfA-15L·P95Δ) were obtained by the same method as that in Case 1 of Example 1. Then, the degradation activity of each of the mouse κ light chain antibodies on R-pNA was evaluated by the same method as that in [Evaluation of enzyme activity] described above, except that R-pNA was used as a substrate.

Figure 7:
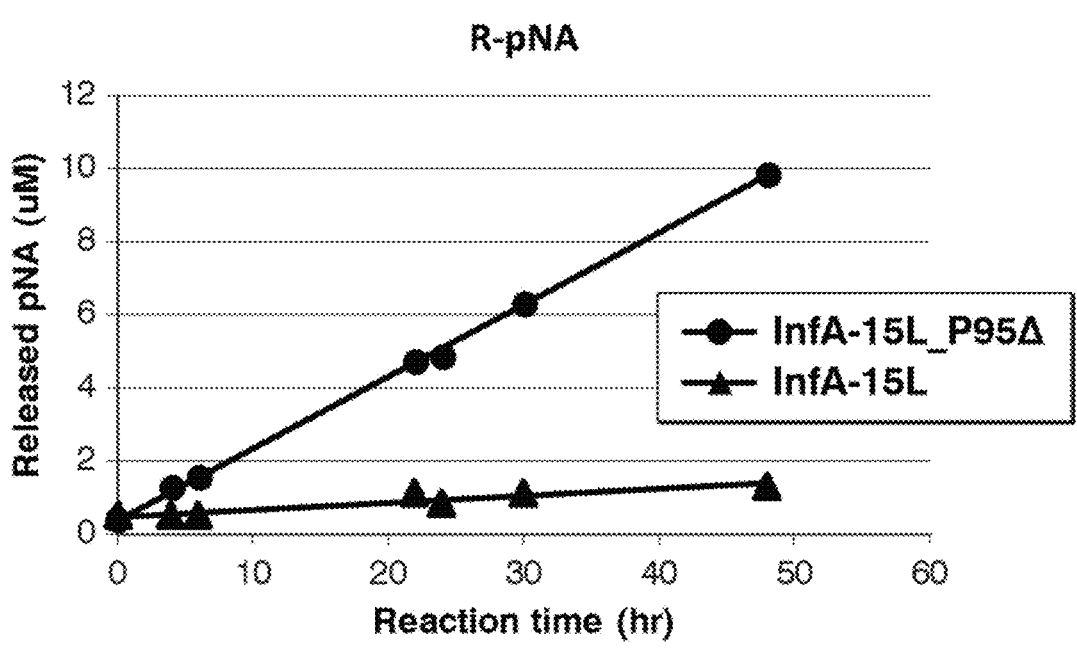
FIG. 7 is a graph showing the temporal change of trypsin-like p-nitroaniline (R-pNA) degradation activity of a mouse κ light chain antibody (InfA-15L) and a mouse κ light chain antibody (InfA-15L P95Δ) in Example 4.

FIG. 7 is a graph showing the temporal change of the R-pNA degradation activity of the mouse κ light chain antibody (InfA-15L) and the mouse κ light chain antibody (InfA-15L·P95Δ). The mouse κ light chain antibody (InfA-15L·P95Δ) increased fluorescence intensity with the passage of time, which shows that this antibody has R-pNA degradation activity. In contrast, substantially no fluorescence was detected from the sample treated with the mouse κ light chain antibody (InfA-15L), which shows that this antibody does not have R-pNA degradation activity. Presumably, this result indicates that the deletion of the proline residue at the 95th position from the N-terminal of a variable region by the Kabat classification in the amino acid sequence of the variable region may also markedly improve the activity of the antibody-enzyme of the mouse κ light chain antibody just as in the human κ light chain antibody.

INDUSTRIAL APPLICABILITY

The present invention can be used in the fields of manufacturing pharmaceutical products containing a human κ light chain antibody as an active ingredient, developing novel anticancer agents, and treating cancer and dementia.

What is claimed is:

1. A method for producing a κ light chain antibody having enzyme activity or improved enzyme activity, the method comprising:

a modification step comprising modifying a polynucleotide that encodes a κ light chain antibody having, as a variable region, a polypeptide having an amino acid sequence in which the 95th amino acid residue from the N-terminal of a variable region by the Kabat classification is a proline residue, by deleting or substituting the proline residue and obtaining a polynucleotide that encodes a κ light chain antibody having, as a variable region, a polypeptide having an amino acid sequence in which the 95th amino acid residue from the N-terminal of a variable region by the Kabat classification is deleted or substituted with an amino acid residue other than a proline residue; and an expression step comprising expressing a κ light chain antibody having enzyme activity in an intracellular or extracellular expression system by using an expression vector including the polynucleotide that encodes a κ light chain antibody obtained after the modification step.

2. The production method according to claim 1, wherein the κ light chain antibody is a human κ light chain antibody or a mouse κ light chain antibody.

3. The production method according to claim 1, wherein a variable region of the κ light chain antibody having enzyme activity or improved enzyme activity is a polypeptide selected from the group consisting of the following (1a) to (3c), (1a) a polypeptide having an amino acid sequence obtained by deletion or substitution of the 95th proline residue from the N-terminal of a variable region by the Kabat classification in an amino acid sequence represented by SEQ ID NO: 1;

(1b) a polypeptide having an amino acid sequence which is obtained by substitution, addition, or deletion of one or more amino acids in the amino acid sequence of the polypeptide (1a) and in which the 95th amino acid residue from the N-terminal of a variable region by the Kabat classification is deleted or substituted with an amino acid residue other than a proline residue;

(1c) a polypeptide having an amino acid sequence which shares 90% or more identity with the amino acid sequence of the polypeptide (1a) and in which the 95th amino acid residue from the N-terminal of a variable region by the Kabat classification is deleted or substituted with an amino acid residue other than a proline residue;

(2a) an amino acid sequence obtained by deletion or substitution of the 95th proline residue from the N-terminal of a variable region by the Kabat classification in an amino acid sequence represented by SEQ ID NO: 2;

(2b) a polypeptide having an amino acid sequence which is obtained by substitution, addition, or deletion of one or more amino acids in the amino acid sequence of the polypeptide (2a) and in which the 95th amino acid residue from the N-terminal of a variable region by the Kabat classification is deleted or substituted with an amino acid residue other than a proline residue;

(2c) a polypeptide having an amino acid sequence which shares 90% or more identity with the amino acid sequence of the polypeptide (2a) and in which the 95th amino acid residue from the N-terminal of a variable region by the Kabat classification is deleted or substituted with an amino acid residue other than a proline residue;

(3a) an amino acid sequence obtained by deletion or substitution of the 95th proline residue from the N-terminal of a variable region by the Kabat classification in an amino acid sequence represented by SEQ ID NO: 3;

(3b) a polypeptide having an amino acid sequence which is obtained by substitution, addition, or deletion of one or more amino acids in the amino acid sequence of the polypeptide (3a) and in which the 95th amino acid residue from the N-terminal of a variable region by the Kabat classification is deleted or substituted with an amino acid residue other than a proline residue;

(3c) a polypeptide having an amino acid sequence which shares 90% or more identity with the amino acid sequence of the polypeptide (3a) and in which the 95th amino acid residue from the N-terminal of a variable region by the Kabat classification is deleted or substituted with an amino acid residue other than a proline residue.

4. The production method according to claim 1, wherein a variable region of the κ light chain antibody having enzyme activity or improved enzyme activity is a polypeptide selected from the group consisting of the following (4a) to (7c), (4a) a polypeptide having an amino acid sequence represented by SEQ ID NO: 4;

(4b) a polypeptide having an amino acid sequence which is obtained by substitution, addition, or deletion of one or more amino acids in the amino acid sequence represented by SEQ ID NO: 4 and in which the 95th amino acid residue from the N-terminal of a variable region by the Kabat classification is deleted or substituted with an amino acid residue other than a proline residue;

(4c) a polypeptide having an amino acid sequence which shares 90% or more identity with the amino acid sequence represented by SEQ ID NO: 4 and in which the 95th amino acid residue from the N-terminal of a variable region by the Kabat classification is deleted or substituted with an amino acid residue other than a proline residue;

(5a) a polypeptide having an amino acid sequence represented by SEQ ID NO: 5;

(5b) a polypeptide having an amino acid sequence which is obtained by substitution, addition, or deletion of one or more amino acids in the amino acid sequence represented by SEQ ID NO: 5 and in which the 95th amino acid residue from the N-terminal of a variable region by the Kabat classification is deleted or substituted with an amino acid residue other than a proline residue;

(5c) a polypeptide having an amino acid sequence which shares 90% or more identity with the amino acid sequence represented by SEQ ID NO: 5 and in which the 95th amino acid residue from the N-terminal of a variable region by the Kabat classification is deleted or substituted with an amino acid residue other than a proline residue;

(6a) a polypeptide having an amino acid sequence represented by SEQ ID NO: 6;

(6b) a polypeptide having an amino acid sequence which is obtained by substitution, addition, or deletion of one or more amino acids in the amino acid sequence represented by SEQ ID NO: 6 and in which the 95th amino acid residue from the N-terminal of a variable region by the Kabat classification is deleted or substituted with an amino acid residue other than a proline residue;

(6c) a polypeptide having an amino acid sequence which shares 90% or more identity with the amino acid sequence represented by SEQ ID NO: 6 and in which the 95th amino acid residue from the N-terminal of a variable region by the Kabat classification is deleted or substituted with an amino acid residue other than a proline residue;

(7a) a polypeptide having an amino acid sequence represented by SEQ ID NO: 7;

(7b) a polypeptide having an amino acid sequence which is obtained by substitution, addition, or deletion of one or more amino acids in the amino acid sequence represented by SEQ ID NO: 7 and in which the 95th amino acid residue from the N-terminal of a variable region by the Kabat classification is deleted or substituted with an amino acid residue other than a proline residue;

(7c) a polypeptide having an amino acid sequence which shares 90% or more identity with the amino acid sequence represented by SEQ ID NO: 7 and in which the 95th amino acid residue from the N-terminal of a variable region by the Kabat classification is deleted or substituted with an amino acid residue other than a proline residue.

5. The production method according to claim 1, wherein a variable region of the κ light chain antibody having enzyme activity or improved enzyme activity is a polypeptide selected from the group consisting of the following (8a) to (8c), (8a) an amino acid sequence obtained by deletion or substitution of the 95th proline residue from the N-terminal of a variable region by the Kabat classification in an amino acid sequence represented by SEQ ID NO: 8;

(8b) a polypeptide having an amino acid sequence which is obtained by substitution, addition, or deletion of one or more amino acids in the amino acid sequence of the polypeptide (8a) and in which the 95th amino acid residue from the N-terminal of a variable region by the Kabat classification is deleted or substituted with an amino acid residue other than a proline residue;

(8c) a polypeptide having an amino acid sequence which shares 90% or more identity with the amino acid sequence of the polypeptide (8a) and in which the 95th amino acid residue from the N-terminal of a variable region by the Kabat classification is deleted or substituted with an amino acid residue other than a proline residue.

6. The production method according to claim 1, wherein a variable region of the κ light chain antibody having enzyme activity is a polypeptide selected from the group consisting of the following (9a) to (9c), (9a) a polypeptide having an amino acid sequence represented by SEQ ID NO: 9;

(9b) a polypeptide having an amino acid sequence which is obtained by substitution, addition, or deletion of one or more amino acids in the amino acid sequence represented by SEQ ID NO: 9 and in which the 95th amino acid residue from the N-terminal of a variable region by the Kabat classification is deleted or substituted with an amino acid residue other than a proline residue;

(9c) a polypeptide having an amino acid sequence which shares 90% or more identity with the amino acid sequence represented by SEQ ID NO: 9 and in which the 95th amino acid residue from the N-terminal of a variable region by the Kabat classification is deleted or substituted with an amino acid residue other than a proline residue.

* * * * *

SEQUENCE LISTING

<160> NUMBER OF SEQ ID NOS: 27

<210> SEQ ID NO 1
<211> LENGTH: 112
<212> TYPE: PRT
<213> ORGANISM: Artificial Sequence
<220> FEATURE:
<223> OTHER INFORMATION: synthetic polypeptide for S35

<400> SEQUENCE: 1

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45
```

-continued

```
Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 2
<211> LENGTH: 112
<212> TYPE: PRT
<213> ORGANISM: Artificial Sequence
<220> FEATURE:
<223> OTHER INFORMATION: synthetic polypeptide for T99

<400> SEQUENCE: 2

Asp Ile Val Met Thr Gln Thr Pro Val Ser Leu Ala Val Thr Pro Gly
1               5                   10                  15

Gln Ser Ala Ser Ile Ser Cys Arg Ser Ser Gln Ser Leu Leu His Gly
            20                  25                  30

Asp Gly Arg Ser Tyr Leu Tyr Trp Tyr Val Gln Arg Pro Gly Gln Ser
        35                  40                  45

Pro Gln Leu Leu Met Tyr Glu Ala Ser Thr Arg Val Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Gly Thr Phe Gly Pro Gly Thr Lys Val Asp Ile Lys
            100                 105                 110

<210> SEQ ID NO 3
<211> LENGTH: 108
<212> TYPE: PRT
<213> ORGANISM: Artificial Sequence
<220> FEATURE:
<223> OTHER INFORMATION: synthetic polypeptide for H55

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Arg Ser Tyr
            20                  25                  30

Val Asn Trp Tyr Gln Gln Lys Pro Gly Lys Ala Pro Arg Leu Leu Ile
        35                  40                  45

Tyr Ala Ala Ser Thr Leu Gln Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Thr Pro Arg
                85                  90                  95

Tyr Thr Phe Gly Gln Gly Thr Lys Leu Asp Ile Lys
            100                 105

<210> SEQ ID NO 4
<211> LENGTH: 112
<212> TYPE: PRT
<213> ORGANISM: Artificial Sequence
```

```
<220> FEATURE:
<223> OTHER INFORMATION: synthetic polypeptide for S34

<400> SEQUENCE: 4

Asp Ile Val Met Thr Gln Ser Pro Leu Ser Leu Pro Val Thr Pro Gly
1               5                   10                  15

Glu Pro Ala Thr Ile Ser Cys Arg Ser Ser Gln Ser Leu Leu His Thr
            20                  25                  30

Asn Gly His Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Lys Phe Ser Gly Ser Gly Ser Gly Thr Asp Phe Thr Leu Lys Ile
65              70                  75                  80

Ser Lys Val Glu Ala Glu Asp Val Gly Val Tyr Tyr Cys Met Gln Ala
                85                  90                  95

Leu His Thr Ser Trp Thr Phe Gly Gln Gly Thr Lys Val Glu Ile Lys
            100                 105                 110

<210> SEQ ID NO 5
<211> LENGTH: 111
<212> TYPE: PRT
<213> ORGANISM: Artificial Sequence
<220> FEATURE:
<223> OTHER INFORMATION: synthetic polypeptide for S38

<400> SEQUENCE: 5

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Ala
                85                  90                  95

Leu Gln Thr Tyr Thr Phe Gly Gln Gly Thr Lys Leu Glu Ile Lys
            100                 105                 110

<210> SEQ ID NO 6
<211> LENGTH: 111
<212> TYPE: PRT
<213> ORGANISM: Artificial Sequence
<220> FEATURE:
<223> OTHER INFORMATION: synthetic polypeptide for T99 P95 deletion

<400> SEQUENCE: 6

Asp Ile Val Met Thr Gln Thr Pro Val Ser Leu Ala Val Thr Pro Gly
1               5                   10                  15

Gln Ser Ala Ser Ile Ser Cys Arg Ser Ser Gln Ser Leu Leu His Gly
            20                  25                  30

Asp Gly Arg Ser Tyr Leu Tyr Trp Tyr Val Gln Arg Pro Gly Gln Ser
        35                  40                  45

Pro Gln Leu Leu Met Tyr Glu Ala Ser Thr Arg Val Ser Gly Val Pro
    50                  55                  60
```

```
Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Gly Thr Phe Gly Pro Gly Thr Lys Val Asp Ile Lys
                100                 105                 110

<210> SEQ ID NO 7
<211> LENGTH: 106
<212> TYPE: PRT
<213> ORGANISM: Artificial Sequence
<220> FEATURE:
<223> OTHER INFORMATION: synthetic polypeptide for H34

<400> SEQUENCE: 7

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Val Leu Ile
                35                  40                  45

Tyr Lys Ala Ser Thr Leu Glu Ser Gly Val Pro Leu Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Thr Tyr Arg Thr
                85                  90                  95

Phe Gly Gln Gly Thr Lys Val Glu Ile Lys
                100                 105

<210> SEQ ID NO 8
<211> LENGTH: 102
<212> TYPE: PRT
<213> ORGANISM: Artificial Sequence
<220> FEATURE:
<223> OTHER INFORMATION: synthetic polypeptide for the InfA-15L

<400> SEQUENCE: 8

Asp Ala Val Met Thr Gln Thr Pro Leu Ser Leu Pro Val Ser Leu Gly
1               5                   10                  15

Asp Gln Ala Ser Ile Ser Cys Arg Ser Ser Pro Ser Leu Glu His Ser
                20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Pro Thr
                100

<210> SEQ ID NO 9
<211> LENGTH: 101
<212> TYPE: PRT
<213> ORGANISM: Artificial Sequence
<220> FEATURE:
<223> OTHER INFORMATION: synthetic polypeptide for the InfA-15L P95del
```

-continued

<400> SEQUENCE: 9

Asp Ala Val Met Thr Gln Thr Pro Leu Ser Leu Pro Val Ser Leu Gly
1               5                   10                  15

Asp Gln Ala Ser Ile Ser Cys Arg Ser Ser Pro Ser Leu Glu His Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Thr
            100

<210> SEQ ID NO 10
<211> LENGTH: 219
<212> TYPE: PRT
<213> ORGANISM: Artificial Sequence
<220> FEATURE:
<223> OTHER INFORMATION: synthetic polypeptide for the whole S35

<400> SEQUENCE: 10

Asp Ile Val Met Thr Gln Ser Pro Leu Ser Leu Pro Val Thr Pro Gly
1               5                   10                  15

Glu Pro Ala Thr Ile Ser Cys Arg Ser Ser Gln Ser Leu Leu His Thr
            20                  25                  30

Asn Gly His Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Lys Phe Ser Gly Ser Gly Ser Gly Thr Asp Phe Thr Leu Lys Ile
65                  70                  75                  80

Ser Lys Val Glu Ala Glu Asp Val Gly Val Tyr Tyr Cys Met Gln Ala
                85                  90                  95

Leu His Thr Ser Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 11
<211> LENGTH: 219
<212> TYPE: PRT

<213> ORGANISM: Artificial Sequence
<220> FEATURE:
<223> OTHER INFORMATION: synthetic polypeptide for the whole S34

<400> SEQUENCE: 11

Asp Ile Val Met Thr Gln Ser Pro Leu Ser Leu Pro Val Thr Pro Gly
1               5                   10                  15

Glu Pro Ala Thr Ile Ser Cys Arg Ser Ser Gln Ser Leu Leu His Thr
            20                  25                  30

Asn Gly His Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Lys Phe Ser Gly Ser Gly Ser Gly Thr Asp Phe Thr Leu Lys Ile
65                  70                  75                  80

Ser Lys Val Glu Ala Glu Asp Val Gly Val Tyr Tyr Cys Met Gln Ala
                85                  90                  95

Leu His Thr Ser Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 12
<211> LENGTH: 218
<212> TYPE: PRT
<213> ORGANISM: Artificial Sequence
<220> FEATURE:
<223> OTHER INFORMATION: synthetic polypeptide for the whole S38

<400> SEQUENCE: 12

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Tyr Thr Phe Gly Gln Gly Thr Lys Leu Glu Ile Lys Arg
            100                 105                 110

-continued

```
Thr Val Ala Ala Pro Ser Val Phe Ile Phe Pro Pro Ser Asp Glu Gln
        115                 120             125

Leu Lys Ser Gly Thr Ala Ser Val Val Cys Leu Leu Asn Asn Phe Tyr
    130                 135             140

Pro Arg Glu Ala Lys Val Gln Trp Lys Val Asp Asn Ala Leu Gln Ser
145                 150             155                 160

Gly Asn Ser Gln Glu Ser Val Thr Glu Gln Asp Ser Lys Asp Ser Thr
                165             170             175

Tyr Ser Leu Ser Ser Thr Leu Thr Leu Ser Lys Ala Asp Tyr Glu Lys
            180             185             190

His Lys Val Tyr Ala Cys Glu Val Thr His Gln Gly Leu Ser Ser Pro
        195             200             205

Val Thr Lys Ser Phe Asn Arg Gly Glu Cys
    210             215
```

```
<210> SEQ ID NO 13
<211> LENGTH: 219
<212> TYPE: PRT
<213> ORGANISM: Artificial Sequence
<220> FEATURE:
<223> OTHER INFORMATION: synthetic polypeptide for the whole T99

<400> SEQUENCE: 13
```

```
Asp Ile Val Met Thr Gln Thr Pro Val Ser Leu Ala Val Thr Pro Gly
1               5                 10                  15

Gln Ser Ala Ser Ile Ser Cys Arg Ser Ser Gln Ser Leu Leu His Gly
            20              25              30

Asp Gly Arg Ser Tyr Leu Tyr Trp Tyr Val Gln Arg Pro Gly Gln Ser
        35              40                  45

Pro Gln Leu Leu Met Tyr Glu Ala Ser Thr Arg Val Ser Gly Val Pro
    50              55                  60

Asp Arg Phe Thr Gly Ser Gly Ser Gly Thr Asp Phe Thr Leu Lys Ile
65              70              75                  80

Ser Arg Val Glu Ala Glu Asp Val Gly Val Tyr Tyr Cys Met Gln Gly
                85              90              95

Thr His Trp Pro Gly Thr Phe Gly Pro Gly Thr Lys Val Asp Ile Lys
            100             105             110

Arg Thr Val Ala Ala Pro Ser Val Phe Ile Phe Pro Pro Ser Asp Glu
        115             120             125

Gln Leu Lys Ser Gly Thr Ala Ser Val Val Cys Leu Leu Asn Asn Phe
    130             135             140

Tyr Pro Arg Glu Ala Lys Val Gln Trp Lys Val Asp Asn Ala Leu Gln
145             150             155                 160

Ser Gly Asn Ser Gln Glu Ser Val Thr Glu Gln Asp Ser Lys Asp Ser
                165             170             175

Thr Tyr Ser Leu Ser Ser Thr Leu Thr Leu Ser Lys Ala Asp Tyr Glu
            180             185             190

Lys His Lys Val Tyr Ala Cys Glu Val Thr His Gln Gly Leu Ser Ser
        195             200             205

Pro Val Thr Lys Ser Phe Asn Arg Gly Glu Cys
    210             215
```

```
<210> SEQ ID NO 14
<211> LENGTH: 218
<212> TYPE: PRT
<213> ORGANISM: Artificial Sequence
<220> FEATURE:
```

<223> OTHER INFORMATION: synthetic polypeptide for the whole T99 P95
    deletion

<400> SEQUENCE: 14

Asp Ile Val Met Thr Gln Thr Pro Val Ser Leu Ala Val Thr Pro Gly
1               5                   10                  15

Gln Ser Ala Ser Ile Ser Cys Arg Ser Ser Gln Ser Leu Leu His Gly
            20                  25                  30

Asp Gly Arg Ser Tyr Leu Tyr Trp Tyr Val Gln Arg Pro Gly Gln Ser
        35                  40                  45

Pro Gln Leu Leu Met Tyr Glu Ala Ser Thr Arg Val Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Gly Thr Phe Gly Pro Gly Thr Lys Val Asp Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 15
<211> LENGTH: 215
<212> TYPE: PRT
<213> ORGANISM: Artificial Sequence
<220> FEATURE:
<223> OTHER INFORMATION: synthetic polypeptide for the whole H55

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Arg Ser Tyr
            20                  25                  30

Val Asn Trp Tyr Gln Gln Lys Pro Gly Lys Ala Pro Arg Leu Leu Ile
        35                  40                  45

Tyr Ala Ala Ser Thr Leu Gln Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Thr Pro Arg
                85                  90                  95

Tyr Thr Phe Gly Gln Gly Thr Lys Leu Asp Ile Lys Arg Thr Val Ala
            100                 105                 110

Ala Pro Ser Val Phe Ile Phe Pro Pro Ser Asp Glu Gln Leu Lys Ser

-continued

```
              115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
    210                 215
```

```
<210> SEQ ID NO 16
<211> LENGTH: 213
<212> TYPE: PRT
<213> ORGANISM: Artificial Sequence
<220> FEATURE:
<223> OTHER INFORMATION: synthetic polypeptide for the whole H34

<400> SEQUENCE: 16

Asp Ile Gln Met Thr Gln Ser Pro Ser Thr Leu Ser Ala Ser Val Gly
1                 5                 10                 15

Asp Arg Val Thr Ile Thr Cys Arg Ala Ser Gln Ser Ile Ser Ser Trp
                20                 25                 30

Leu Ala Trp Tyr Gln Gln Lys Pro Gly Lys Ala Pro Lys Val Leu Ile
            35                 40                 45

Tyr Lys Ala Ser Thr Leu Glu Ser Gly Val Pro Leu Arg Phe Ser Gly
    50                 55                 60

Ser Gly Ser Gly Thr Glu Phe Thr Leu Thr Ile Ser Ser Leu Gln Pro
65                 70                 75                 80

Asp Asp Phe Ala Thr Tyr Tyr Cys Gln Gln Tyr Ser Thr Tyr Arg Thr
                85                 90                 95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
    210
```

```
<210> SEQ ID NO 17
<211> LENGTH: 219
<212> TYPE: PRT
<213> ORGANISM: Artificial Sequence
<220> FEATURE:
<223> OTHER INFORMATION: synthetic polypeptide for the whole InfA-15L
```

-continued

<400> SEQUENCE: 17

Asp Ala Val Met Thr Gln Thr Pro Leu Ser Leu Pro Val Ser Leu Gly
1               5                   10                  15

Asp Gln Ala Ser Ile Ser Cys Arg Ser Ser Pro Ser Leu Glu His Ser
                20                  25                  30

Asn Gly Asn Thr Tyr Leu Asn Trp Tyr Leu Gln Lys Pro Gly Gln Ser
            35                  40                  45

Pro Gln Leu Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Pro Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 18
<211> LENGTH: 218
<212> TYPE: PRT
<213> ORGANISM: Artificial Sequence
<220> FEATURE:
<223> OTHER INFORMATION: synthetic polypeptide for the whole InfA-15L
      P95del

<400> SEQUENCE: 18

Asp Ala Val Met Thr Gln Thr Pro Leu Ser Leu Pro Val Ser Leu Gly
1               5                   10                  15

Asp Gln Ala Ser Ile Ser Cys Arg Ser Ser Pro Ser Leu Glu His Ser
                20                  25                  30

Asn Gly Asn Thr Tyr Leu Asn Trp Tyr Leu Gln Lys Pro Gly Gln Ser
            35                  40                  45

Pro Gln Leu Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

-continued

```
Leu Thr Ser Gly Gly Ala Ser Val Val Cys Phe Leu Asn Asn Phe Tyr
    130             135             140

Pro Lys Asp Ile Asn Val Lys Trp Lys Ile Asp Gly Ser Glu Arg Gln
145             150             155             160

Asn Gly Val Leu Asn Ser Trp Thr Asp Gln Asp Ser Lys Asp Ser Thr
            165             170             175

Tyr Ser Met Ser Ser Thr Leu Thr Leu Thr Lys Asp Glu Tyr Glu Arg
            180             185             190

His Asn Ser Tyr Thr Cys Glu Ala Thr His Lys Thr Ser Thr Ser Pro
        195             200             205

Ile Val Lys Ser Phe Asn Arg Asn Glu Cys
    210             215
```

```
<210> SEQ ID NO 19
<211> LENGTH: 219
<212> TYPE: PRT
<213> ORGANISM: Homo sapiens

<400> SEQUENCE: 19
```

```
Asp Val Val Met Thr Gln Ser Pro Leu Ser Leu Pro Val Thr Pro Gly
1               5               10              15

Glu Pro Ala Ser Ile Ser Cys Arg Ser Ser Gln Ser Leu Leu His Ser
            20              25              30

Asn Gly Tyr Asn Tyr Leu Asp Trp Tyr Leu Gln Lys Pro Gly Gln Ser
            35              40              45

Pro Gln Leu Leu Ile Tyr Leu Gly Ser Asn Arg Ala Ser Gly Val Pro
    50              55              60

Asp Arg Phe Ser Gly Ser Gly Ser Gly Thr Asp Phe Thr Leu Lys Ile
65              70              75              80

Ser Arg Val Glu Ala Glu Asp Val Gly Val Tyr Tyr Cys Met Gln Ala
            85              90              95

Leu Gln Thr Pro Arg Thr Phe Gly Gln Gly Thr Lys Val Glu Ile Lys
            100             105             110

Arg Thr Val Ala Ala Pro Ser Val Phe Ile Phe Pro Pro Ser Asp Glu
            115             120             125

Gln Leu Lys Ser Gly Thr Ala Ser Val Val Cys Leu Leu Asn Asn Phe
    130             135             140

Tyr Pro Arg Glu Ala Lys Val Gln Trp Lys Val Asp Asn Ala Leu Gln
145             150             155             160

Ser Gly Asn Ser Gln Glu Ser Val Thr Glu Gln Asp Ser Lys Asp Ser
            165             170             175

Thr Tyr Ser Leu Ser Ser Thr Leu Thr Leu Ser Lys Ala Asp Tyr Glu
            180             185             190

Lys His Lys Leu Tyr Ala Cys Glu Val Thr His Gln Gly Leu Ser Ser
        195             200             205

Pro Val Thr Lys Ser Phe Asn Arg Gly Glu Cys
    210             215
```

```
<210> SEQ ID NO 20
<211> LENGTH: 8
<212> TYPE: PRT
<213> ORGANISM: Artificial Sequence
<220> FEATURE:
<223> OTHER INFORMATION: synthetic polypeptide for histidine-tag

<400> SEQUENCE: 20
```

-continued

```
Leu Glu His His His His His His
1               5

<210> SEQ ID NO 21
<211> LENGTH: 8
<212> TYPE: PRT
<213> ORGANISM: Homo sapiens

<400> SEQUENCE: 21

Ser Asn Lys Gly Ala Ile Ile Gly
1               5

<210> SEQ ID NO 22
<211> LENGTH: 18
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: X is phosphorylated serine
<220> FEATURE:
<221> NAME/KEY: MISC_FEATURE
<222> LOCATION: (14)..(14)
<223> OTHER INFORMATION: X is phosphorylated serine

<400> SEQUENCE: 22

Glu Ile Val Tyr Lys Xaa Pro Val Val Ser Gly Asp Thr Xaa Pro Arg
1               5                   10                  15

His Leu

<210> SEQ ID NO 23
<211> LENGTH: 18
<212> TYPE: PRT
<213> ORGANISM: Homo sapiens

<400> SEQUENCE: 23

Gly Ala Ile Ser Leu Ala Pro Lys Ala Gln Ile Lys Glu Ser Leu Arg
1               5                   10                  15

Ala Glu

<210> SEQ ID NO 24
<211> LENGTH: 100
<212> TYPE: PRT
<213> ORGANISM: Homo sapiens

<400> SEQUENCE: 24

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 25
```

-continued

```
<211> LENGTH: 95
<212> TYPE: PRT
<213> ORGANISM: Homo sapiens

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 26
<211> LENGTH: 95
<212> TYPE: PRT
<213> ORGANISM: Homo sapiens

<400> SEQUENCE: 26

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 27
<211> LENGTH: 214
<212> TYPE: PRT
<213> ORGANISM: Artificial Sequence
<220> FEATURE:
<223> OTHER INFORMATION: synthetic polypeptide for the whole H34_P95(+)

<400> SEQUENCE: 27

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Val Leu Ile
            35                  40                  45

Tyr Lys Ala Ser Thr Leu Glu Ser Gly Val Pro Leu Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Thr Tyr Pro Arg
                85                  90                  95

Thr Phe Gly Gln Gly Thr Lys Val Glu Ile Lys Arg Thr Val Ala Ala
```

-continued

```
          100              105                 110

Pro Ser Val Phe Ile Phe Pro Pro Ser Asp Glu Gln Leu Lys Ser Gly
        115                120                 125

Thr Ala Ser Val Val Cys Leu Leu Asn Asn Phe Tyr Pro Arg Glu Ala
    130                135                140

Lys Val Gln Trp Lys Val Asp Asn Ala Leu Gln Ser Gly Asn Ser Gln
145                150                   155                   160

Glu Ser Val Thr Glu Gln Asp Ser Lys Asp Ser Thr Tyr Ser Leu Ser
            165                170                   175

Ser Thr Leu Thr Leu Ser Lys Ala Asp Tyr Glu Lys His Lys Val Tyr
            180                185                190

Ala Cys Glu Val Thr His Gln Gly Leu Ser Ser Pro Val Thr Lys Ser
        195                200                   205

Phe Asn Arg Gly Glu Cys
    210
```